(12) United States Patent
Romanov

(10) Patent No.: US 10,533,211 B2
(45) Date of Patent: *Jan. 14, 2020

(54) COUMARIN COMPOUNDS AND THEIR USES AS FLUORESCENT LABELS

(71) Applicant: Illumina Cambridge Limited, Cambridge (GB)

(72) Inventor: Nikolai Nikolaevich Romanov, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,783

(22) Filed: Feb. 22, 2019

(65) Prior Publication Data

US 2019/0185918 A1    Jun. 20, 2019

Related U.S. Application Data

(63) Continuation of application No. 15/851,014, filed on Dec. 21, 2017, now Pat. No. 10,214,768.

(60) Provisional application No. 62/438,006, filed on Dec. 22, 2016.

(51) Int. Cl.
| | |
|---|---|
| *C12Q 1/6816* | (2018.01) |
| *C09K 11/06* | (2006.01) |
| *C07D 491/147* | (2006.01) |
| *C07H 19/10* | (2006.01) |
| *C07H 19/14* | (2006.01) |
| *C07D 491/04* | (2006.01) |
| *C12Q 1/6876* | (2018.01) |
| *C07H 21/00* | (2006.01) |
| *C12Q 1/6869* | (2018.01) |
| *C07D 491/052* | (2006.01) |

(52) U.S. Cl.
CPC ......... *C12Q 1/6816* (2013.01); *C07D 491/04* (2013.01); *C07D 491/052* (2013.01); *C07D 491/147* (2013.01); *C07H 19/10* (2013.01); *C07H 19/14* (2013.01); *C07H 21/00* (2013.01); *C09K 11/06* (2013.01); *C12Q 1/6869* (2013.01); *C12Q 1/6876* (2013.01); *C09K 2211/1018* (2013.01)

(58) Field of Classification Search
CPC .. C12Q 1/6816; C12Q 1/6869; C12Q 1/6876; C07D 491/04; C07D 491/052; C07D 491/147; C07H 19/10; C07H 19/14; C07H 21/00; C09K 11/06; C09K 2211/1018
USPC ....................................................... 435/6.11
See application file for complete search history.

(56) References Cited

U.S. PATENT DOCUMENTS

| | | | |
|---|---|---|---|
| 5,302,509 A | 4/1994 | Cheeseman | |
| 6,093,518 A * | 7/2000 | Imai ........................ | C08F 2/50 430/287.1 |
| 6,172,218 B1 | 1/2001 | Brënner | |
| 6,465,178 B2 | 10/2002 | Chappa et al. | |
| 6,727,362 B1 | 4/2004 | Lai et al. | |
| 10,214,768 B2 * | 2/2019 | Romanov ............ | C07D 491/04 |
| 2013/0079232 A1 | 3/2013 | Kain et al. | |
| 2014/0079923 A1 | 3/2014 | George et al. | |
| 2014/0220588 A1 | 8/2014 | Hell et al. | |

FOREIGN PATENT DOCUMENTS

| | | |
|---|---|---|
| DE | 21 26 811 A1 | 12/1972 |
| EP | 1535969 A2 | 6/2005 |
| JP | 2013231165 A * | 11/2013 |
| WO | WO 98/44151 | 10/1998 |
| WO | WO 00/06770 | 2/2000 |
| WO | WO 00/18957 | 4/2000 |
| WO | WO 00/31148 | 6/2000 |
| WO | WO 00/53812 | 9/2000 |
| WO | WO 01/01143 | 1/2001 |
| WO | WO 01/57248 | 8/2001 |
| WO | WO 02/12566 | 2/2002 |
| WO | WO 03/014392 | 2/2003 |
| WO | WO 03/074519 A1 | 9/2003 |
| WO | WO 2004/018493 | 3/2004 |
| WO | WO 2004/018497 | 3/2004 |
| WO | WO 2005/024010 | 3/2005 |
| WO | WO 2005/047301 | 5/2005 |
| WO | WO 2005/065814 | 7/2005 |
| WO | WO 2006/026368 A2 | 3/2006 |
| WO | WO 2006/120433 | 11/2006 |
| WO | WO 2007/020457 | 2/2007 |
| WO | WO 2007/135368 | 11/2007 |
| WO | WO 2009/124800 A1 | 10/2009 |
| WO | WO 2010/074325 A1 | 7/2010 |
| WO | WO 2012/152698 A1 | 11/2012 |
| WO | WO 2014/139596 | 9/2014 |

OTHER PUBLICATIONS

Margulies et al. 2005. Genome sequencing in open microfabricated high density picoliter reactors. *Nature*, 437:376-380.
Scheit, K. H. (1980). *Nucleotide analogs: Synthesis and biological function*. New York: John Wiley & Sons, TOC, 5 pages.
Shendure et al. 2005. Accurate multiplex polony sequencing of an evolved bacterial genome. *Science*, 309(5741):1728-1732.
Uhlman et al. 1990. Antisense oligonucleotides: A new therapeutic principle. *Chemical Reviews*, 90(4):543-584.
Anufrik et al. 1999. New laser media based on bifluorophore coumarin molecules. *Journal of Applied Spectroscopy*, 66(5):772-779.
CAS Registry No. 811785-95-2 Pyridinium, 1-(5-carboxpentyl)-4-[8,9-dihydro-6,8,8-trimethyl-2-oxo-9-(3-sulfopropyl)-2H-pyrano[3,2-g]quinolin-3-yl]-, inner salt, 2005.

(Continued)

*Primary Examiner* — Kristin A Vajda
(74) *Attorney, Agent, or Firm* — Knobbe, Martens, Olson & Bear, LLP

(57) ABSTRACT

The present application relates to new coumarin compounds and their uses as fluorescent labels. The compounds may be used as fluorescent labels for nucleotides in nucleic acid sequencing applications.

23 Claims, 3 Drawing Sheets

(56) References Cited

OTHER PUBLICATIONS

Grabolle et al. 2016. Highly fluorescent dye-nanoclay hybrid materials made from different dye classes. *American Chemical Society, Langmuir*, 32:3506-3513.

Kauffman et al. 2001. Synthesis of julolidine derivatives. *Organic Preparations and Procedures International*, 33(6):603-613.

Moylan, C. R. 1994. Molecular hyperpolarizabilities of coumarin dyes. *J. Phys. Chem.*, 98:13513-13516.

Nizamov et al. 2012. Phosphorylated 3-heteroarylcoumarins and their use in fluorescence microscopy and nanoscopy. *Chemistry, A European Journal*, 18:16339-16348.

Nizamov et al. 2016. "Reduced" coumarin dyes with an O-phosphorylated 2,2-dimethyl-4-(hydroxymethyl)-1,2,3,4-tetrahydroquinoline fragment: Synthesis, spectra, and STED microscopy. *Chemistry, A European Journal*, 22:11631-11642.

Ohzono et al. 2016. Fluorescence microscopy reveals molecular localisation at line defects in nematic liquid crystals. www.nature.com/scientificreports, 6:36477, 9 pages.

Schiedel et al. 2001. Single-compound libraries of organic materials: Parallel synthesis and screening of fluorescent dyes. *Angew. Chem. Int. Ed.*, 40(24):4677-4680.

Schill et al. 2013. 4-Trifluoromethyl-substituted coumarins with large stokes shifts: Synthesis, bioconjugates, and their use in super-resolution fluorescence microscopy. *Chemistry, A European Journal*, 19:16556-16565.

International Search Report and Written Opinion dated Feb. 15, 2018 for International Application No. PCT/EP2017/083128 filed Dec. 15, 2017, 15 pages.

Nizamov, et al., "Phosphorylated 3-Heteroarylcoumarins and Their Use in Fluorescence Microscopy and Nanoscopy", *Chemistry: A European Journal*, pp. 1-41, 2012.

Schill, et al., "4-Trifluoromethyl-Substituted Coumarins with Large Stokes Shifts: Synthesis, Bioconjugates, and Their Use in Super-Resolution Fluorescence Microscopy", *Chemistry: A European Journal*, pp. 1-18, 2013.

* cited by examiner

COUMARIN COMPOUNDS AND THEIR USES AS FLUORESCENT LABELS

INCORPORATION BY REFERENCE TO ANY PRIORITY APPLICATIONS

The present application is a continuation of U.S. application Ser. No. 15/851,014, filed Dec. 21, 2017 and to be issued as U.S. Pat. No. 10,214,768 on Feb. 26, 2019, which claims the benefit of priority to U.S. Provisional Application No. 62/438,006, filed Dec. 22, 2016, each of which is incorporated by reference in its entirety.

BACKGROUND

Field

The present application relates to coumarin compounds. The compounds may be used as fluorescent labels, particularly for nucleotide labeling in nucleic acid sequencing applications.

Background

Non-radioactive detection of nucleic acids utilizing fluorescent labels is an important technology in molecular biology. Many procedures employed in recombinant DNA technology previously relied on the use of nucleotides or polynucleotides radioactively labeled with, for example $^{32}P$. Radioactive compounds permit sensitive detection of nucleic acids and other molecules of interest. However, there are serious limitations in the use of radioactive isotopes such as their expense, limited shelf life and more importantly safety considerations. Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced to simplify experimental protocols and facilitate the production of application-specific reagent kits. In multi-color automated DNA sequencing systems for example, multiplex fluorescent detection allows for the analysis of several different nucleotide bases in a single electrophoresis lane. This increases throughput over detection systems using a single-color, and also can reduce the uncertainties associated with inter-lane electrophoretic mobility variations.

However, multiplex fluorescent detection can be problematic and there are a number of important factors, which constrain selection of fluorescent labels. First, it is difficult to find dye compounds whose absorption and emission spectra are suitably spectrally resolved. In addition, when several fluorescent dyes are used together, simultaneous excitation may be difficult because the absorption bands of the dyes for different spectral regions may be widely separated. Many excitation methods use high power lasers and therefore the dye must have sufficient photo-stability to withstand such laser excitation. A final consideration of particular importance in molecular biology methods is that the fluorescent dyes must be compatible with the reagent chemistries. Thus, for example the fluorescent dyes used in DNA synthesis or sequencing reactions must be compatible with the solvents and reagents, buffers, polymerase enzymes and ligase enzymes used in those reactions. In one example, PCT Publication No. WO 2007/135368 describes a class of rhodamine compounds used as fluorescent labels.

Coumarin dyes family has attracted attention of chemists due to their remarkable spectral properties. Nevertheless, there are only a few photo-stable fluorescent dyes with large Stokes shifts (LSS) that are commercially available. Most of these dyes also contain the coumarin fragment as a scaffold. For example, most of the dyes from Dyomics are coumarin derivatives absorbing at about 480-520 nm, and emitting in the region of 560-630. Other examples of this class of coumarin dyes include phosphorylated coumarin based dyes as disclosed in U.S. Publication No. 2014/0220588 and commercially available dyes Star440SXP and Star 470SXP from Abberior. Another practically useful coumarin dye is AlexaFluor™ 430 with absorption and emission maxima at 434 nm and 539 nm respectively. Other LSS fluorescent dyes include Pacific Orange™ (abs. 390 nm, emission 540 nm; Stokes shift 150 nm, Invitrogen) and BD Horizon™ V500 (abs. 415 nm, emission 500 nm; Stokes shift 85 nm, BD Biosciences) Chromeo™ 494 (abs. 494 nm, emission 628 nm, Stokes Shift 134 nm, Active Motive).

SUMMARY

Described herein are novel coumarin derivatives and their use as bio-molecule labels, particularly as labels for nucleotides used in nucleic acid sequencing. When such dyes are used for the preparation of bio-molecule conjugates, improvements can be seen in the length, intensity and quality of sequencing read obtainable due to the use of these new fluorescent compounds.

Some embodiments described herein are related to coumarin compounds of Formula (I), salts or mesomeric forms thereof:

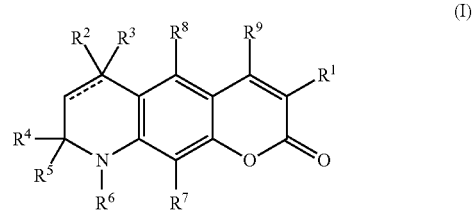

wherein $R^1$ is

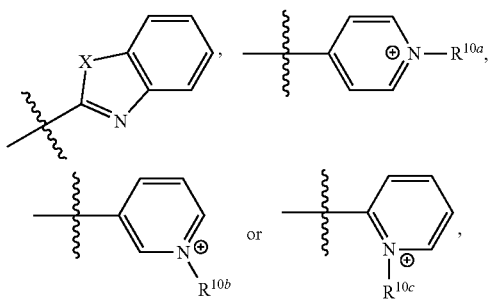

and wherein $R^1$ is optionally substituted with one or more substituents selected from the group consisting of alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted aryl, optionally substituted heteroaryl, optionally substituted cycloalkyl, and optionally substituted heterocyclyl;

each $R^2$, $R^3$, $R^4$, $R^5$, and $R^9$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

each $R^6$, $R^{10a}$, $R^{10b}$ and $R^{10c}$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

each $R^7$ and $R^8$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

alternatively, $R^6$ and $R^7$ together with the atoms to which they are attached form a ring or ring system selected from the group consisting of optionally substituted 5-10 membered heteroaryl or optionally substituted 5-10 membered heterocyclyl;

X is selected from the group consisting of O, S, $NR^{11}$, and Se;

$R^{11}$ is selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and the bond represented by a solid and dashed line ------ is selected from the group consisting of a single bond and a double bond, provided that when ------ is a double bond, then $R^3$ is absent.

Some embodiments described herein are related to fluorescent compounds of Formula (II) with a Stokes shift at least about 60 nm, salts, or mesomeric forms thereof:

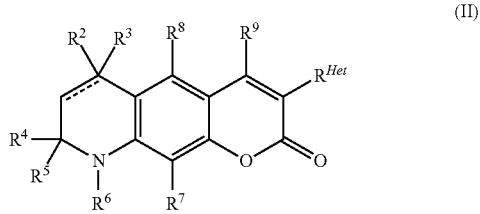

(II)

wherein $R^{Het}$ is a 5 to 10 membered heteroaryl optionally substituted with one or more $R^{10}$;

each $R^1$, $R^2$, $R^3$, $R^4$, and $R^5$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

$R^6$ is selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

each $R^7$ and $R^8$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, $R^6$ and $R^7$ together with the atoms to which they are attached form a ring or ring system selected from the group consisting of optionally substituted 5-10 membered heteroaryl or optionally substituted 5-10 membered heterocyclyl;

each $R^{10}$ is independently selected from the group consisting of alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

the bond represented by a solid and dashed line ------ is selected from the group consisting of a single bond and a double bond, provided that when ------ is a double bond, then $R^3$ is absent.

Some embodiments described herein are related to nucleotide or oligonucleotide labeled with a compound of Formula (I) or Formula (II).

Some embodiments described herein are related to kits containing one or more nucleotides where at least one nucleotide is a labeled nucleotide described herein.

Some further embodiments described herein are related to methods of sequencing including incorporating a labeled nucleotide described herein in a sequencing assay, and detecting the labeled nucleotide.

DETAILED DESCRIPTION

Figure 1:
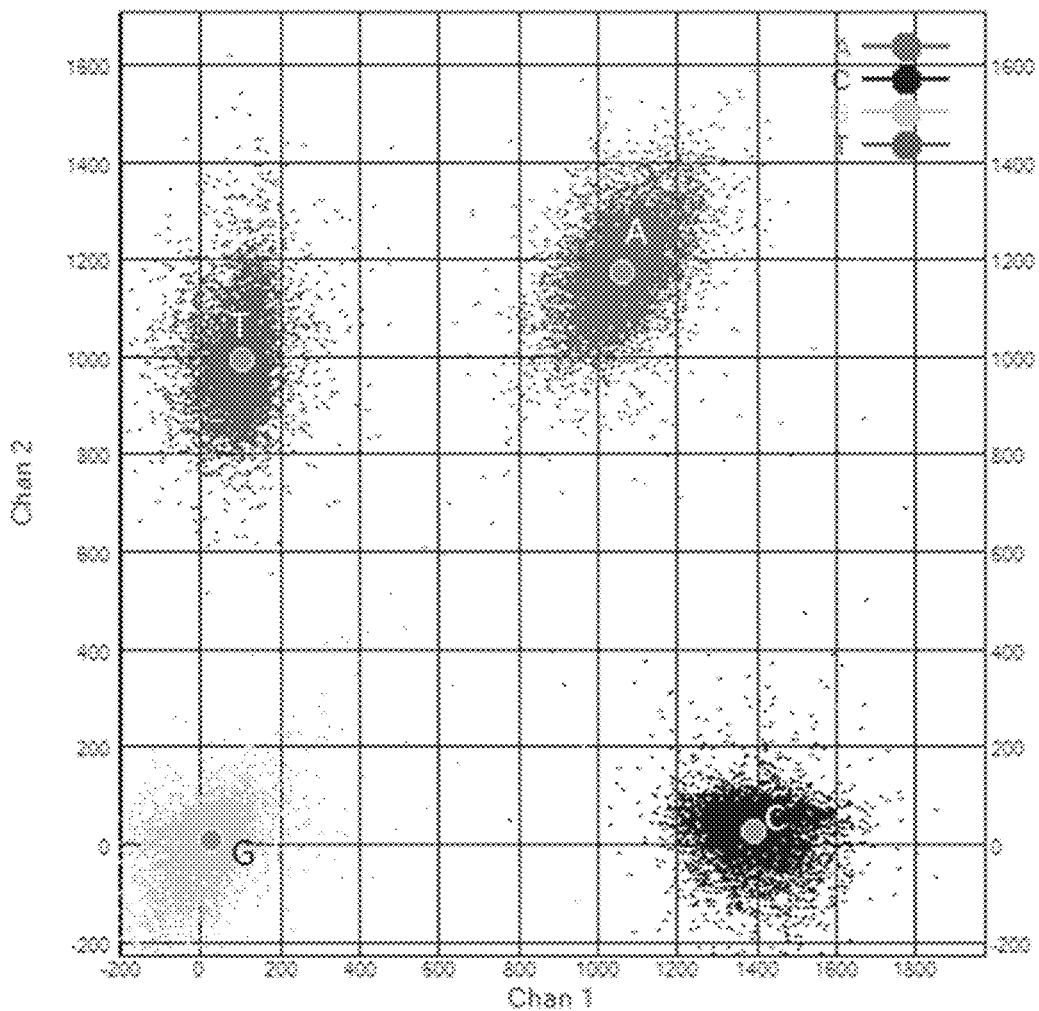
FIG. 1 illustrates the usability of the A-nucleotide labeled with the new coumarin dye I-16 as described herein for sequencing analysis.

Embodiments described herein relate to new coumarin dyes and their derivatives of the structure of Formula (I) for use as fluorescent labels. Further embodiments relate to fluorescent compound of the structure of Formula (II) with a Stokes shift of at least about 60 nm.

These new fluorescent dyes may be used as fluorescent labels, particularly for nucleotide labeling in nucleic acid sequencing applications. Methods of preparing these fluorescent dyes and downstream sequencing applications utilizing these dyes are also exemplified.

Surprisingly, it has been discovered that the fluorescence intensities of the new dyes and their bio-conjugates are nearly equal when irradiated with either blue or green light sources. For example, when the dyes are excited with 460 nm (blue) and 540 nm (green) laser or LED, the fluorescence intensities are about the same in some cases. As described below, this property holds true in solution and on flow cells, enabling simplified sequencing analysis with high quality.

Compounds of Formula (I)

Some embodiments described herein are related to new coumarin derivatives of Formula (I), or salts, mesomeric forms thereof:

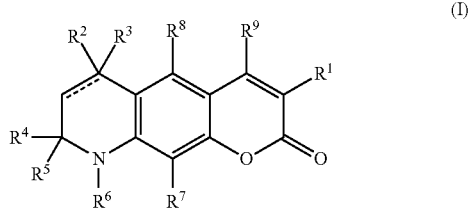

wherein $R^1$ is

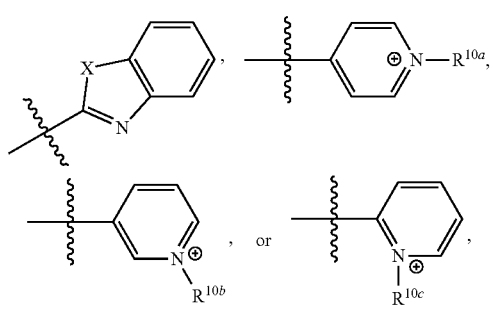

and wherein $R^1$ is optionally substituted with one or more substituents selected from the group consisting of alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted aryl, optionally substituted heteroaryl, optionally substituted cycloalkyl, and optionally substituted heterocyclyl;

each $R^2$, $R^3$, $R^4$, $R^5$, and $R^9$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

each $R^6$, $R^{10a}$, $R^{10b}$ and $R^{10c}$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

each $R^7$ and $R^8$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

alternatively, $R^6$ and $R^7$ together with the atoms to which they are attached form a ring or ring system selected from the group consisting of optionally substituted 5-10 membered heteroaryl or optionally substituted 5-10 membered heterocyclyl;

X is selected from the group consisting of O, S, $NR^{11}$, and Se;

$R^{11}$ is selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and the bond represented by a solid and dashed line ===== is selected from the group consisting of a single bond and a double bond, provided that when ===== is a double bond, then $R^3$ is absent.

In some embodiments of the compounds of Formula (I), the alkyl or substituted alkyl disclosed herein is $C_{1-12}$ alkyl, or more preferably $C_{1-6}$ alkyl. In some embodiments, the alkoxy disclosed herein is $C_{1-12}$ alkoxy, or more preferably $C_{1-6}$ alkoxy. In some embodiments, the alkenyl and alkynyl groups disclosed herein are $C_{2-6}$ alkenyl and $C_{2-6}$ alkynyl. In some embodiments, the haloalkyl, haloalkoxy, aminoalkyl, hydroxyalkyl, heteroalkyl groups disclosed herein are $C_{1-12}$ haloalkyl, $C_{1-12}$ haloalkoxy, $C_{1-12}$ aminoalkyl, $C_{1-12}$ hydroxyalkyl and $C_{1-12}$ heteroalkyl; more preferably $C_{1-6}$ haloalkyl, $C_{1-6}$ haloalkoxy, $C_{1-6}$ aminoalkyl, $C_{1-6}$ hydroxyalkyl and $C_{1-6}$ heteroalkyl. In some embodiments, the alkoxyalkyl group disclosed herein is $C_{1-6}$ alkoxy($C_{1-6}$ alkyl). In some embodiments, the optionally substituted aryl disclosed herein is optionally substituted $C_{6-10}$ aryl, for example, phenyl. In some embodiments, the optionally substituted heteroaryl disclosed herein is optionally substituted 5-10 membered heteroaryl; more preferably, optionally substituted 5-6 membered heteroaryl. In some embodiments, the optionally substituted carbocyclyl disclosed herein is optionally substituted 3-7 membered carbocyclyl, in particular 3-7 membered cycloalkyl. In some embodiments, optionally substituted heterocyclyl disclosed herein are optionally substituted 3-7 membered heterocyclyl, more preferably 5-6 membered heterocyclyl.

In some embodiments of the compounds of Formula (I), any of $R^2$ through $R^9$ may be selected from an alkyl substituted with one or more substituents selected from carboxyl (—CO$_2$H) or carboxylate (CO$_2^-$), sulfo (SO$_3$H) or sulfonate (SO$_3^-$) groups. In some such embodiments, the compounds of Formula (I) are also represented by its salt form Formula (I') with an organic or inorganic cation:

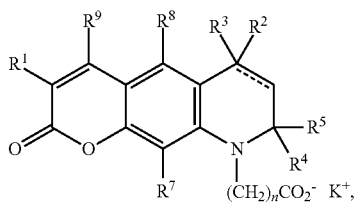

(I')

wherein K is an organic or inorganic cation, and n is an integer selected from 1 to 20.

In some embodiments of the compounds of Formula (I) or (I'), $R^1$ is

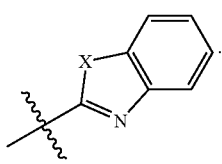

In some such embodiments, X is O. In some other embodiments, X is O. In some such embodiments, the compounds of Formula (I) are also represented by Formula (Ia):

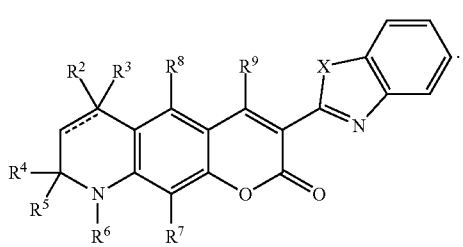

(Ia)

In some embodiments, $R^1$ is substituted with one or more substituents selected from the group consisting of alkyl, halo, and C-carboxy. In one embodiment, $R^1$ is substituted with a chloro (i.e., —Cl). In another embodiment, $R^1$ is substituted with a carboxyl (i.e., —C(O)OH).

In some embodiments of the compounds of Formula (I) or (I'), $R^1$ is

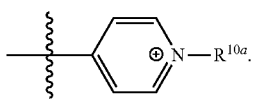

In some other embodiments, $R^1$ is

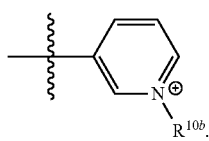

It is understood that when $R^{10a}$, $R^{10b}$ or $R^{10c}$ is connected to a pyridyl group bearing a positive charge on the nitrogen atom, $R^{10a}$, $R^{10b}$ or $R^{10c}$ may contain a negative charge so that $R^1$ as a whole is charge neutral. Alternatively, when $R^{10a}$, $R^{10b}$ or $R^{10c}$ is connected to a pyridyl group bearing a positive charge on the nitrogen atom, the compound described herein may contain a counterion so that the compound as a whole is charge neutral. In some such embodiments, $R^{10a}$, $R^{10b}$ or $R^{10c}$ is a substituted alkyl, for example, substituted $C_1$, $C_2$, $C_3$, $C_4$, $C_5$, or $C_6$ alkyl. In some such embodiment, the alkyl is substituted with carboxyl (—$CO_2H$), carboxylate ($CO_2^-$), sulfo ($SO_3H$), or sulfonate ($SO_3^-$). In some such embodiments, the compounds of Formula (I) are also represented by Formula (Ib) and (Ic) or their salt Formula (Ib') and (Ic'):

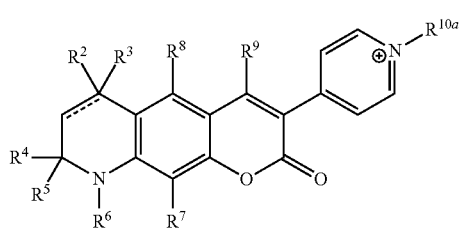

(Ib)

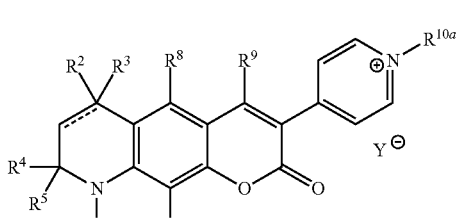

(Ib')

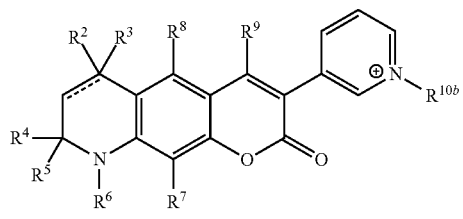

(Ic)

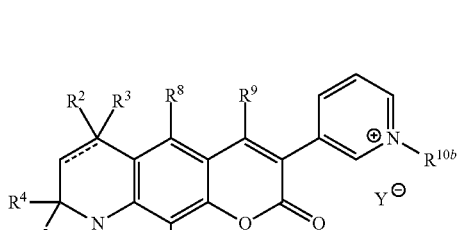

(Ic')

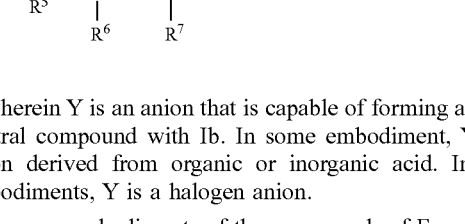

wherein Y is an anion that is capable of forming a charge neutral compound with Ib. In some embodiment, Y is an anion derived from organic or inorganic acid. In some embodiments, Y is a halogen anion.

In some embodiments of the compounds of Formula (I), (I'), (Ia), (Ib), (Ib'), (Ic), or (Ic'), the bond represented by a solid and dashed line ===== is a double bond and the compounds are also presented by Formula (I-1), (I'-1), (Ia-1), (Ib-1), (Ib'-1), (Ic-1), or (Ic'-1):

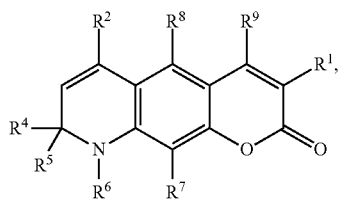
(I-1)

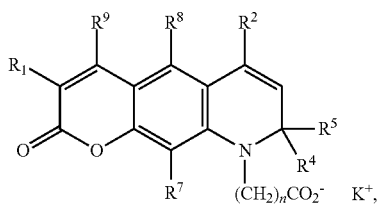
(I'-1)

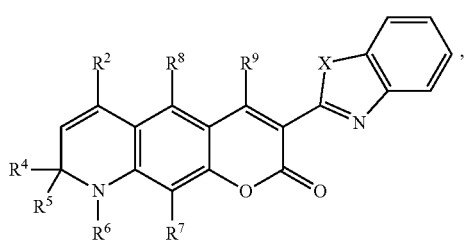
(Ia-1)

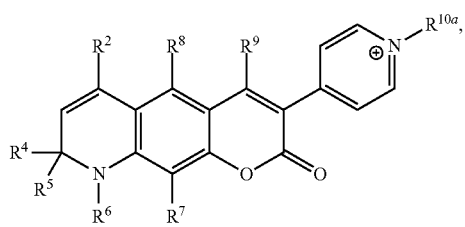
(Ib-1)

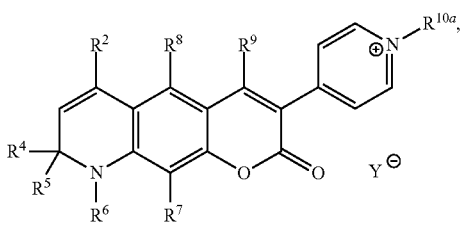
(Ib'-1)

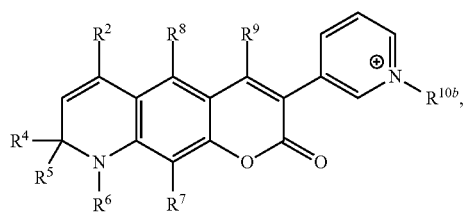
(Ic-1)

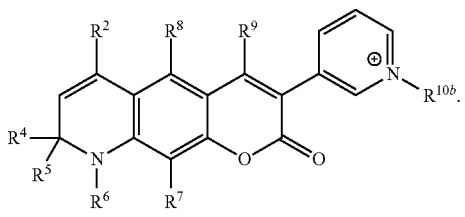
(Ic'-1)

In some embodiments of the compounds of Formula (I), (I-1), (I'-1), (Ia-1), (Ib-1), (Ib'-1), (Ic-1), or (Ic'-1), $R^2$ is alkyl. In one embodiment, $R^2$ is methyl. In some other embodiments, $R^2$ is H.

In some embodiments of the compounds of Formula (I), (I-1), (I'-1), (Ia-1), (Ib-1), (Ib'-1), (Ic-1), or (Ic'-1), at least one of $R^4$ and $R^5$ is alkyl. In some such embodiments, each $R^4$ and $R^5$ is alkyl. In one embodiment, both $R^4$ and $R^5$ are methyl. In some alternative embodiments, at least one of $R^4$ and $R^5$ is H. In one such embodiment, both $R^4$ and $R^5$ are H.

In some embodiments of the compounds of Formula (I), (I'), (Ia), (Ib) or (Ib'), the bond represented by a solid and dashed line ----- is a single bond and the compounds are also presented by Formula (I-2), (I'-2), (Ia-2), (Ib-2), (Ib'-2), (Ic-2), or (Ic'-2):

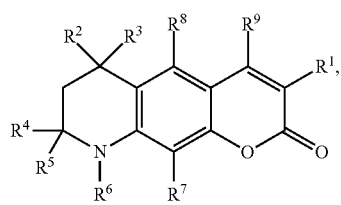
(I-2)

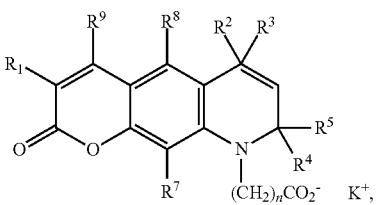
(I'-2)

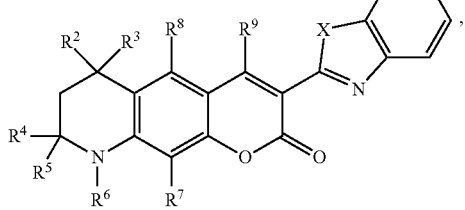
(Ia-2)

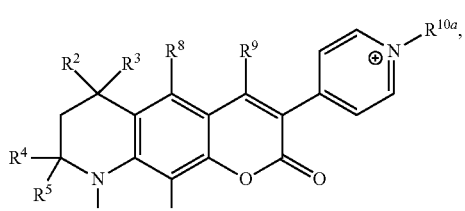
(Ib-2)

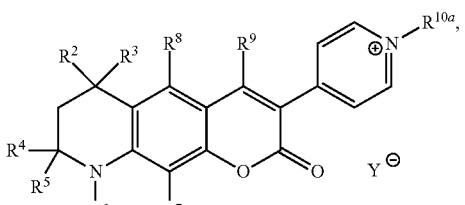
(Ib'-2)

-continued

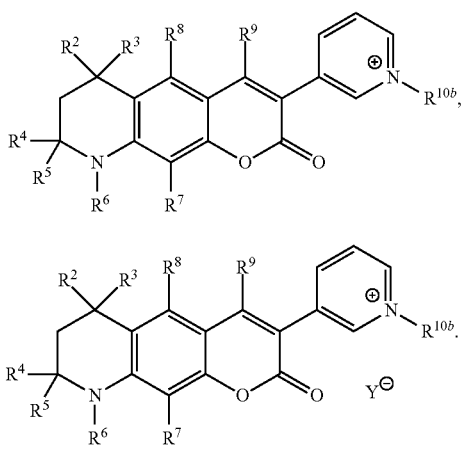

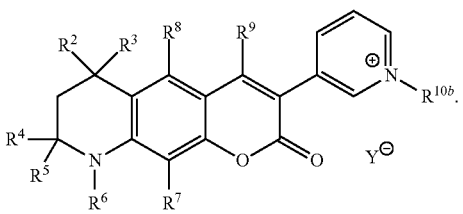

In some embodiments of the compounds of Formula (I), (I-2), (I'-2), (Ia-2), (Ib-2), (Ib'-2), (Ic-2), or (Ic'-2), at least one of $R^2$ and $R^3$ is alkyl. In some further embodiments, both $R^2$ and $R^3$ are alkyl. In one embodiment, both $R^2$ and $R^3$ are methyl. In some other embodiments, at least one of $R^2$ and $R^3$ is H. In one embodiment, both $R^2$ and $R^3$ are H.

In some embodiments of the compounds of Formula (I), (I-2), (I'-2), (Ia-2), (Ib-2), (Ib'-2), (Ic-2), or (Ic'-2), at least one of $R^4$ and $R^5$ is H. In one such embodiment, both $R^4$ and $R^5$ are H. In some alternative embodiments, at least one of $R^4$ and $R^5$ is alkyl. In some such embodiments, each $R^4$ and $R^5$ is alkyl. In one embodiment, both $R^4$ and $R^5$ are methyl.

In some embodiments of the compounds of Formula (I), (I'), (I-1), (I'-1), (Ia-1), (Ib-1), (Ib'-1), (Ic-1), (Ic'-1), (1-2), (I'-2), (Ia-2), (Ib-2), (Ib'-2), (Ic-2), or (Ic'-2), $R^6$ is a substituted alkyl, for example, substituted $C_1$, $C_2$, $C_3$, $C_4$, $C_5$, or $C_6$ alkyl. In one embodiment, $R^6$ is alkyl substituted with carboxyl. In some embodiments, $R^6$ is an alkyl substituted with —C(O)OR$^{12}$, and wherein R$^{12}$ is selected from the group consisting of optionally substituted alkyl, optionally substituted aryl, optionally substituted heteroaryl, and optionally substituted 3 to 7 membered cycloalkyl. In one such embodiment, R$^{12}$ is an alkyl, for example, methyl, ethyl, or t-butyl. In some further embodiments, $R^6$ is an alkyl substituted with —C(O)NR$^{13}$R$^{14}$, and wherein each R$^{13}$ and R$^{14}$ is independently selected from H, optionally substituted alkyl, optionally substituted aryl, optionally substituted heteroaryl and optionally substituted 3 to 7 membered cycloalkyl. In some further embodiments, R$^{13}$ and R$^{14}$ is independently selected from an alkyl substituted with one or more substituents selected from the group consisting of carboxyl, carboxylate, —C(O)OR$^{11}$, sulfo and sulfonate.

In some embodiments of the compounds of Formula (I), (I'), (I-1), (I'-1), (Ia-1), (Ib-1), (Ib'-1), (Ic-1), (Ic'-1), (I-2), (I'-2), (Ia-2), (Ib-2), (Ib'-2), (Ic-2), or (Ic'-2), $R^7$ is H.

In some alternative embodiments of the compounds of Formula (I), (I'), (I-1), (I'-1), (Ia-1), (Ib-1), (Ib'-1), (I-2), (I'-2), (Ia-2), (Ib-2), or (Ib'-2), $R^6$ and $R^7$ are joined together with the atoms to which they are attached to form an optionally substituted 3 to 10 membered heterocyclyl, for example, an optionally substituted 6 membered heterocyclyl. In some such embodiments, the optionally substituted heterocyclyl contains one heteroatom. In some such embodiments, the optionally substituted heterocyclyl is substituted with one or more alkyls, for example, methyl.

In some embodiments of the compounds of Formula (I), (I'), (I-1), (I'-1), (Ia-1), (Ib-1), (Ib'-1), (Ic-1), (Ic'-1), (I-2), (I'-2), (Ia-2), (Ib-2), (Ib'-2), (Ic-2), or (Ic'-2), $R^8$ is H.

In some embodiments of the compounds of Formula (I), (I'), (I-1), (I'-1), (Ia-1), (Ib-1), (Ib'-1), (Ic-1), (Ic'-1), (I-2), (I'-2), (Ia-2), (Ib-2), (Ib'-2), (Ic-2), or (Ic'-2), $R^9$ is H.

In some specific embodiments, exemplary compounds of Formula (I) include Compounds I-1 through I-20 and Compounds I-22 through I-32 as shown in Table 1 below:

TABLE 1

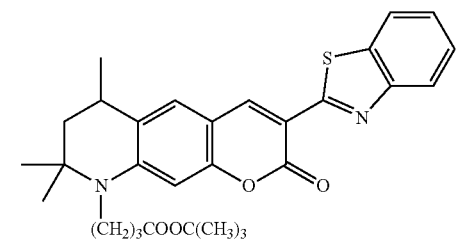

I-1

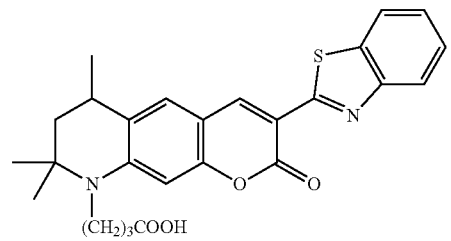

I-2

TABLE 1-continued
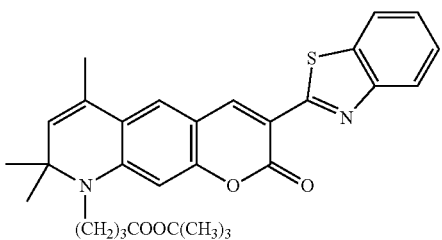
I-3
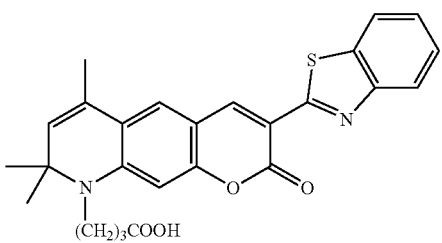
I-4
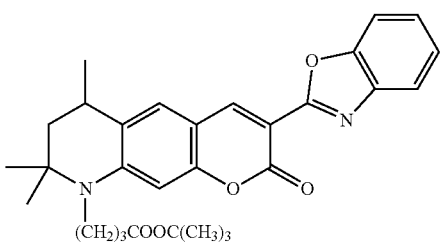
I-5
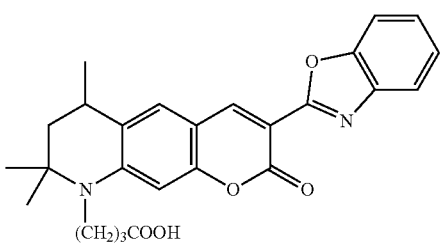
I-6
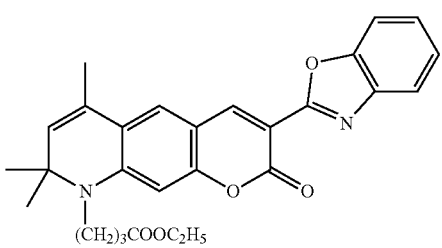
I-7
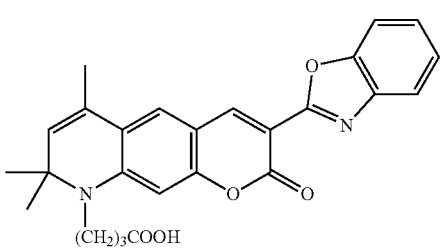
I-8

TABLE 1-continued
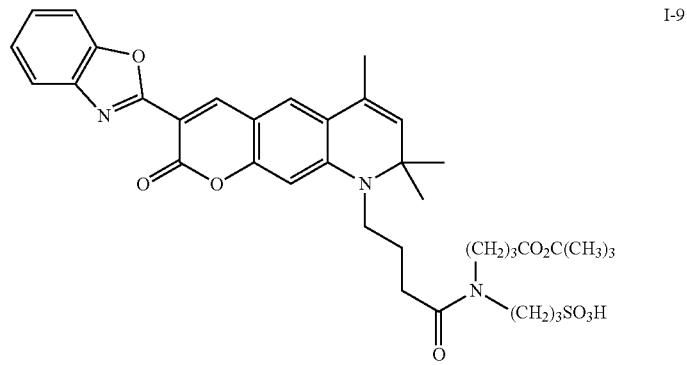
I-9
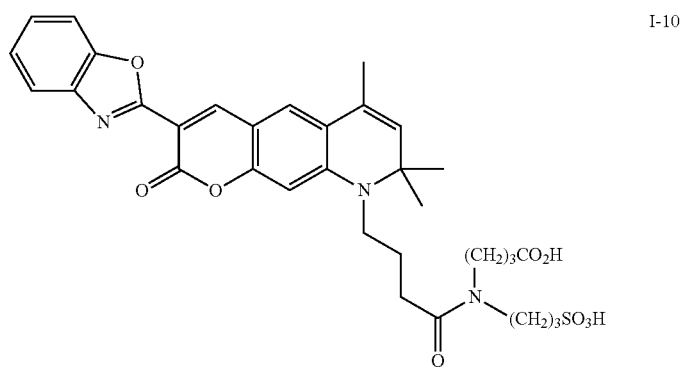
I-10
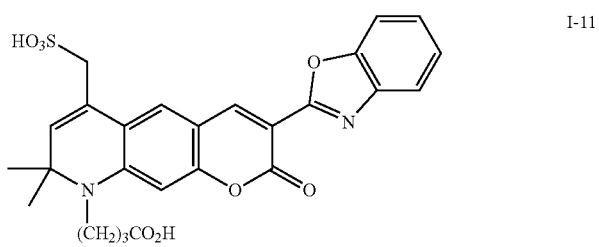
I-11
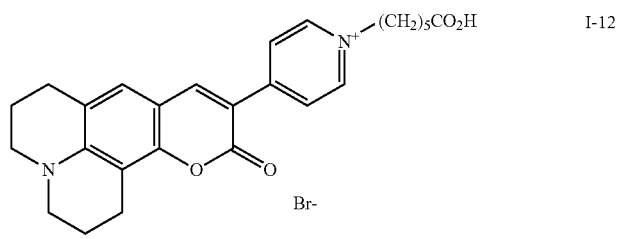
I-12
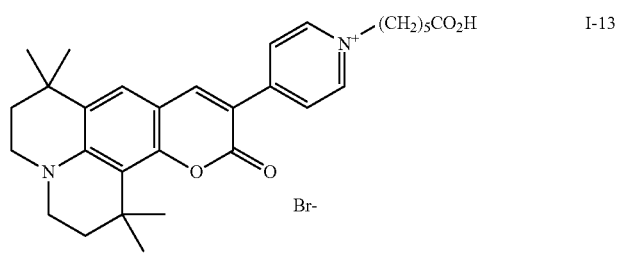
I-13

TABLE 1-continued
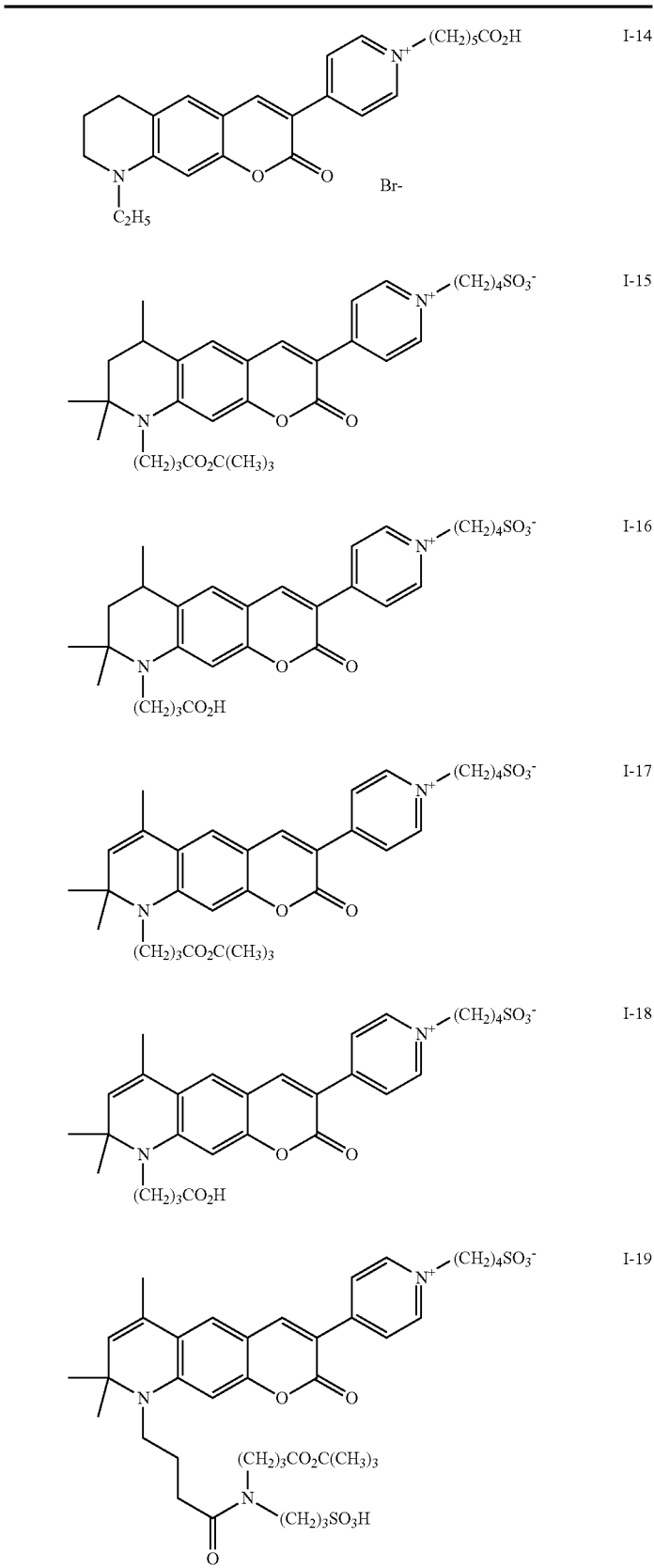

TABLE 1-continued
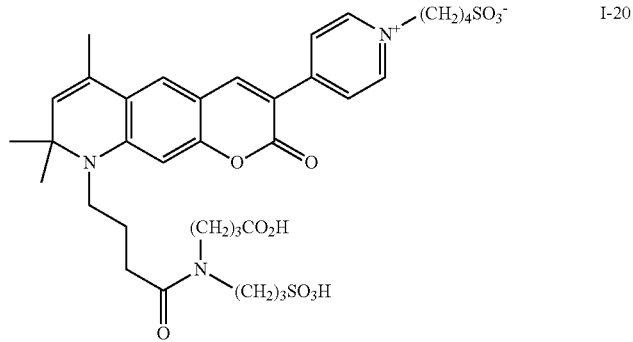
I-20
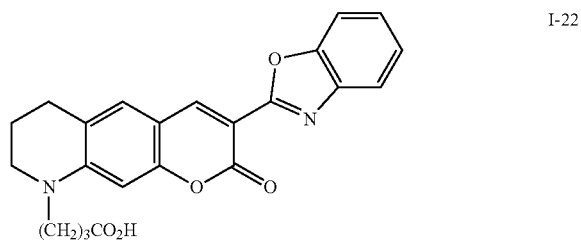
I-22
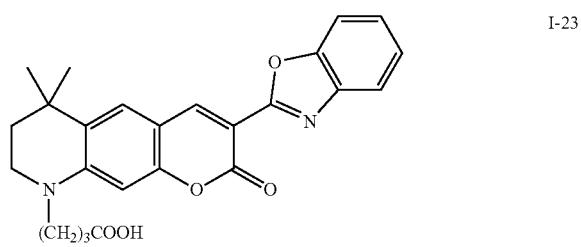
I-23
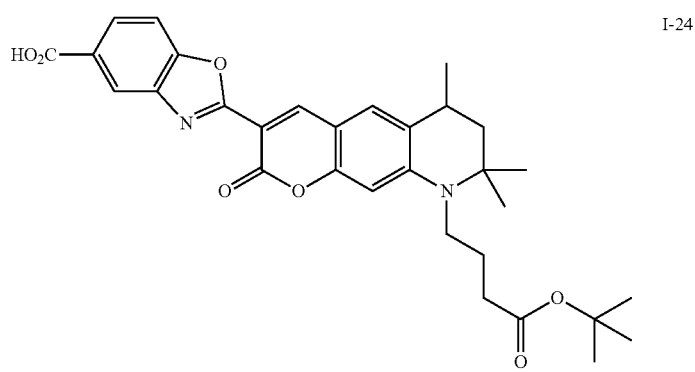
I-24
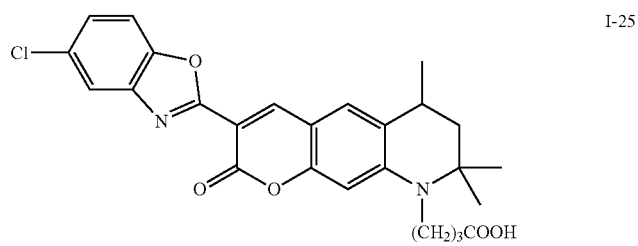
I-25

TABLE 1-continued
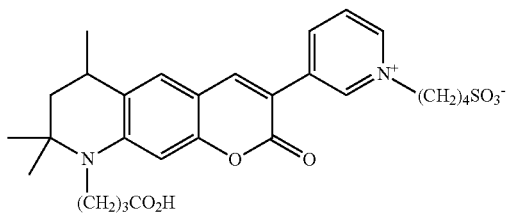
I-26
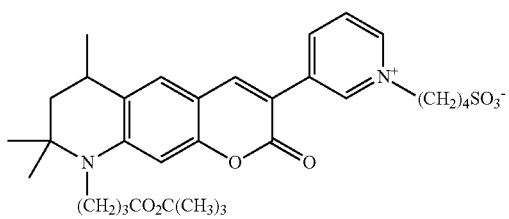
I-27
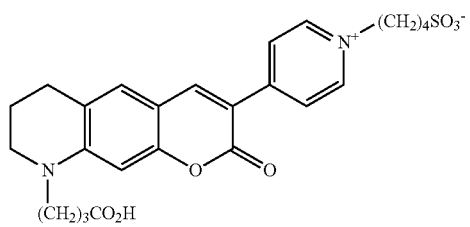
I-28
I-29
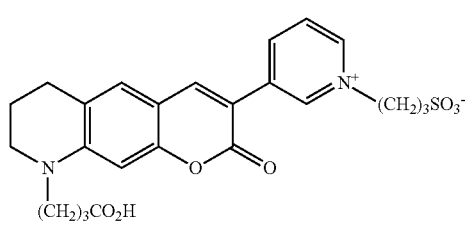
I-30
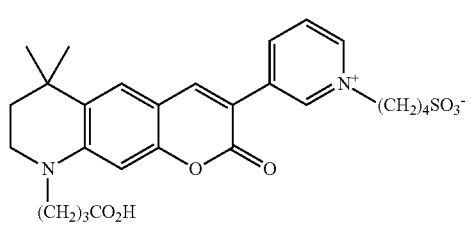
I-31
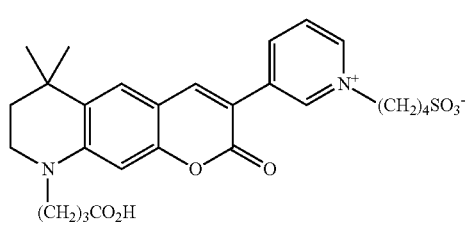
I-32

In some embodiments of the compounds of Formula (I), the compound is covalently attached to a nucleotide or oligonucleotide via $R^6$, and wherein $R^6$ is a substituted alkyl, for example, a substituted $C_1$, $C_2$, $C_3$, $C_4$, $C_5$, or $C_6$ alkyl. In one embodiment, $R^6$ is an alkyl substituted with carboxyl.

In some alternative embodiments, the compound is covalently attached to a nucleotide or oligonucleotide via $R^8$, and wherein $R^8$ is a substituted alkyl, for example, a substituted $C_1$, $C_2$, $C_3$, $C_4$, $C_5$, or $C_6$ alkyl. In one embodiment, $R^8$ is an alkyl substituted with carboxyl.

In some alternative embodiments, the compound is covalently attached to a nucleotide or oligonucleotide via $R^{10a}$, $R^{10b}$, or $R^{10c}$, and wherein each of $R^{10a}$, $R^{10b}$, or $R^{10c}$ is a substituted alkyl, for example, a substituted $C_1$, $C_2$, $C_3$, $C_4$, $C_5$, or $C_6$ alkyl. In one embodiment, each of $R^{10a}$, $R^{10b}$, or $R^{10c}$ is an alkyl substituted with carboxyl.

In some embodiments, the structure of compound of Formula (I) is represented in one or more mesomeric forms:

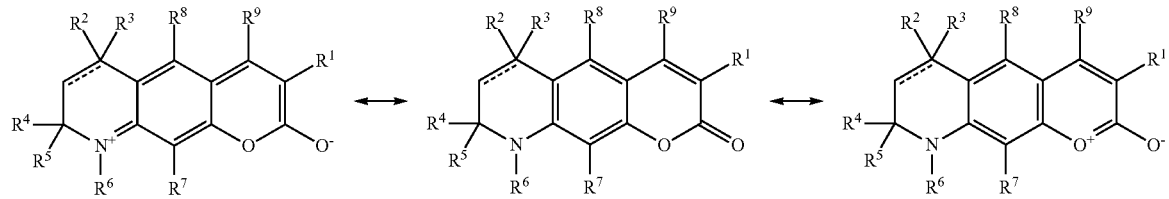

Compounds of Formula (II)

Some embodiments described herein are related to fluorescent compounds of Formula (II) with a Stokes shift at least about 60 nm, or salts, mesomeric forms thereof:

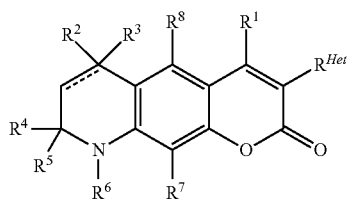

(II)

wherein $R^{Het}$ is a 5 to 10 membered heteroaryl optionally substituted with one or more $R^{10}$;

each $R^1$, $R^2$, $R^3$, $R^4$, and $R^5$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

$R^6$ is selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

each $R^7$ and $R^8$ is independently selected from the group consisting of H, alkyl, substituted alkyl, alkoxy, alkenyl, alkynyl, haloalkyl, haloalkoxy, alkoxyalkyl, amino, amino- alkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

alternatively, $R^6$ and $R^7$ together with the atoms to which they are attached form a ring or ring system selected from the group consisting of optionally substituted 5-10 membered heteroaryl or optionally substituted 5-10 membered heterocyclyl;

each $R^{10}$ is independently selected from the group consisting of alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

the bond represented by a solid and dashed line ===== is selected from the group consisting of a single bond and a double bond, provided that when ===== is a double bond, then $R^3$ is absent.

In some embodiments, the fluorescent compounds of Formula (II) have a Stokes shift ranging from about 60 nm to about 100 nm, or from about 60 nm to about 90 nm.

In some embodiments of the compounds of Formula (II), the alkyl or substituted alkyl disclosed herein is $C_{1-12}$ alkyl, or more preferably $C_{1-6}$ alkyl. In some embodiments, the alkoxy disclosed herein is $C_{1-12}$ alkoxy, or more preferably $C_{1-6}$ alkoxy. In some embodiments, the alkenyl and alkynyl groups disclosed herein are $C_{2-6}$ alkenyl and $C_{2-6}$ alkynyl. In some embodiments, the haloalkyl, haloalkoxy, aminoalkyl, hydroxyalkyl, heteroalkyl groups disclosed herein are $C_{1-12}$ haloalkyl, $C_{1-12}$ haloalkoxy, $C_{1-12}$ aminoalkyl, $C_{1-12}$ hydroxyalkyl and $C_{1-12}$ heteroalkyl; more preferably $C_{1-6}$ haloalkyl, $C_{1-6}$ haloalkoxy, $C_{1-6}$ aminoalkyl, $C_{1-6}$ hydroxyalkyl and $C_{1-6}$ heteroalkyl. In some embodiments, the alkoxyalkyl group disclosed herein is $C_{1-6}$ alkoxy($C_{1-6}$ alkyl). In some embodiments, the optionally substituted aryl disclosed herein is optionally substituted $C_{6-10}$ aryl, for example, phenyl. In some embodiments, the optionally substituted heteroaryl disclosed herein is optionally substituted 5-10 membered heteroaryl; more preferably, optionally substituted 5-6 membered heteroaryl. In some embodiments, the optionally substituted carbocyclyl disclosed herein is optionally substituted 3-7 membered carbocyclyl, in particular 3-7 membered cycloalkyl. In some embodiments, optionally substituted heterocyclyl disclosed herein are optionally substituted 3-7 membered heterocyclyl, more preferably 5-6 membered heterocyclyl.

In some embodiments of the compounds of Formula (II), any of $R^1$ through $R^8$ may be selected from an alkyl substituted with one or more substituents selected from carboxyl ($-CO_2H$) or carboxylate ($CO_2^-$), sulfo ($SO_3H$) or sulfonate ($SO_3^-$) groups. In some such embodiments, the substituted alkyl is a substituted $C_1$, $C_2$, $C_3$, $C_4$, $C_5$, or $C_6$ alkyl. In some such embodiments, the compounds of Formula (II) are also represented by its salt form Formula (II') with an organic or inorganic cation:

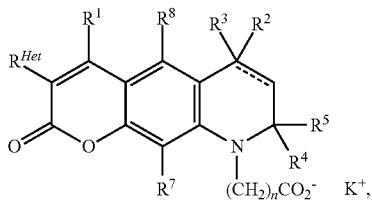

(II')

wherein K is an organic or inorganic cation, and n is an integer selected from 1 to 20.

In some embodiments of the compounds of Formula (II) or (II'), $R^{Het}$ is a 9 membered heteroaryl optionally substituted with one or more $R^{10}$. In some such embodiments, $R^{Het}$ is selected from optionally substituted benzothiazolyl or benzoxazolyl, for example, 2-benzothiazolyl or 2-benzoxazolyl. In some other embodiments, $R^{Het}$ is a 6 membered heteroaryl optionally substituted with one or more $R^{10}$. In one such embodiment, $R^{Het}$ is an substituted pyridyl, for example, 4-pyridyl with the structure:

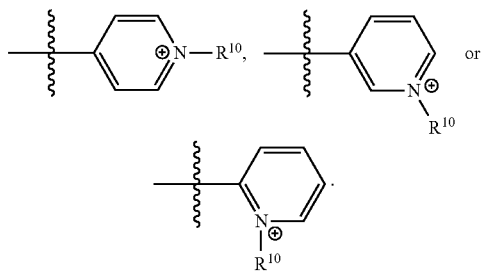

It is understood that when $R^{10}$ is connected to a pyridyl group bearing a positive charge on the nitrogen atom, $R^{10}$ may contain a negative charge so that $R^{Het}$ as a whole is charge neutral. Alternatively, when $R^{10}$ is connected to a pyridyl group bearing a positive charge on the nitrogen atom, the compound described herein may contain a counterion so that the compound as a whole is charge neutral. In some such embodiments, $R^{10}$ is a substituted alkyl, for example, substituted $C_1$, $C_2$, $C_3$, $C_4$, $C_5$, or $C_6$ alkyl. In some such embodiment, $R^{10}$ is substituted with carboxyl (—$CO_2H$), carboxylate ($CO_2^-$), sulfo ($SO_3H$), or sulfonate ($SO_3^-$).

In some embodiments of the compounds of Formula (II) or (II'), the bond represented by a solid and dashed line ------ in Formula (II) is a double bond and the compounds are also represented by Formula (II-1) or (II'-1):

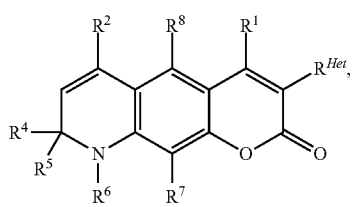

(II-1)

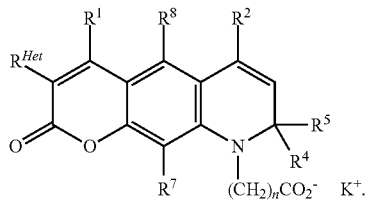

(II'-1)

In some embodiments of the compounds of Formula (II), (II'), (II-1) or (II'-1), $R^2$ is alkyl. In one embodiment, $R^2$ is methyl. In some other embodiments, $R^2$ is H.

In some embodiments of the compounds of Formula (II), (II'), (II-1) or (II'-1), at least one of $R^4$ and $R^5$ is alkyl. In some such embodiments, each $R^4$ and $R^5$ is alkyl. In one embodiment, both $R^4$ and $R^5$ are methyl. In some alternative embodiments, at least one of $R^4$ and $R^5$ is H. In one such embodiment, both $R^4$ and $R^5$ are H.

In some embodiments of the compounds of Formula (II) or (II'), the bond represented by a solid and dashed line ------ is a single bond and the compounds are also presented by Formula (II-2) or (II'-2):

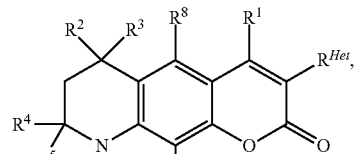

(II-2)

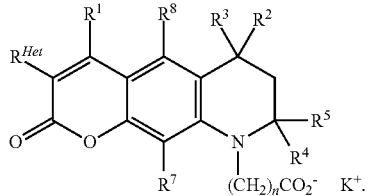

(II'-2)

In some embodiments of the compounds of Formula (II), (II'), (II-2) or (II'-2), at least one of $R^2$ and $R^3$ is alkyl. In some further embodiments, both $R^2$ and $R^3$ are alkyl. In one embodiment, both $R^2$ and $R^3$ are methyl. In some other embodiments, at least one of $R^2$ and $R^3$ is H. In one embodiment, both $R^2$ and $R^3$ are H.

In some embodiments of the compounds of Formula (II), (II'), (II-2) or (II'-2), at least one of $R^4$ and $R^5$ is H. In one such embodiment, both $R^4$ and $R^5$ are H. In some alternative embodiments, at least one of $R^4$ and $R^5$ is alkyl. In some such embodiments, each $R^4$ and $R^5$ is alkyl. In one embodiment, both $R^4$ and $R^5$ are methyl.

In some embodiments of the compounds of Formula (II), (II'), (II-1), (II'-1), (II-2) or (II'-2), $R^6$ is a substituted alkyl, for example, substituted $C_1$, $C_2$, $C_3$, $C_4$, $C_5$, or $C_6$ alkyl. In one embodiment, $R^6$ is alkyl substituted with carboxyl. In some embodiments, $R^6$ is an alkyl substituted with —C(O)OR$^{12}$, and wherein $R^{12}$ is selected from the group consisting of optionally substituted alkyl, optionally substituted aryl, optionally substituted heteroaryl, and optionally substituted 3 to 7 membered cycloalkyl. In one such embodiment, $R^{12}$ is an alkyl, for example, methyl, ethyl, or t-butyl. In some further embodiments, $R^6$ is an alkyl substituted with —C(O)

$NR^{13}R^{14}$, and wherein each $R^{13}$ and $R^{14}$ is independently selected from H, optionally substituted alkyl, optionally substituted aryl, optionally substituted heteroaryl and optionally substituted 3 to 7 membered cycloalkyl. In some further embodiments, $R^{13}$ and $R^{14}$ is independently selected from an alkyl substituted with one or more substituents selected from the group consisting of carboxyl, carboxylate, —C(O)OR$^{11}$, sulfo and sulfonate.

In some embodiments of the compounds of Formula (II), (II'), (II-1), (II'-1), (II-2) or (II'-2), $R^7$ is H.

In some alternative embodiments of the compounds of Formula (II), (II'), (11-1), (II'-1), (11-2) or (II'-2), $R^6$ and $R^7$ are joined together with the atoms to which they are attached to form an optionally substituted 3 to 10 membered heterocyclyl, for example, an optionally substituted 6 membered heterocyclyl. In some such embodiments, the optionally substituted heterocyclyl contains one heteroatom. In some such embodiments, the optionally substituted heterocyclyl is substituted with one or more alkyl, for example, methyl.

In some embodiments of the compounds of Formula (II), (II'), (II-1), (II'-1), (II-2) or (II'-2), $R^1$ is H.

In some embodiments of the compounds of Formula (II), (II'), (II-1), (II'-1), (II-2) or (II'-2), $R^8$ is H.

As understood by one of ordinary skill in the art, when a compound of Formula (I) or (II) contains positively or negatively charged substituent groups, it may also contains a negatively or positively charged counterion such that the compound as a whole is neutral.

Definition

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:
Ac Acetyl
Ac$_2$O Acetic anhydride
aq. Aqueous
BOC or Boc tert-Butoxycarbonyl
BOP (Benzotriazol-1-yloxy)tris(dimethylamino)phosphonium hexafluorophosphate
cat. Catalytic
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP(s) Dideoxynucleotide(s)
DCM Methylene chloride
DMA Dimethylacetamide
DMF Dimethylformamide
Et Ethyl
EtOAc Ethyl acetate
ffC Fully functionalized Nucleotide Conjugate
g Gram(s)
h or hr Hour(s)
IPA Isopropyl Alcohol
LCMS Liquid chromatography-mass spectrometry
MeCN Acetonitrile
mL Milliliter(s)
PG Protecting group
Ph Phenyl
ppt Precipitate
PyBOP (Benzotriazol-1-yloxy)tripyrrolidinophosphonium hexafluorophosphate
RT, rt Room temperature
SBS Sequencing by Synthesis
TEA Triethylamine
TEAB Tetraethylammonium bromide
TFA Trifluoroacetic acid
TRIS Tris(hydroxymethyl)aminomethane
Tert, t tertiary
THF Tetrahydrofuran
TLC Thin Layer Chromatography
TSTU O—(N-Succinimidyl)-N,N,N',N'-tetramethyluronium tetrafluoroborate
μL Microliter(s)

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{14}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_{2-6}$ alkenyl" or similar designations. By way of example only, "$C_{2-6}$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_{2-6}$ alkynyl" or similar designations. By way of example only, "$C_{2-6}$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_{1-6}$ heteroalkyl" or similar designations. The heteroalkyl group may contain one or more heteroatoms. By way of example only, "$C_{1-6}$ heteroalkyl" indicates that there are one to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "sulfonyl" group refers to an "—SO₂R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfo" or "sulfonyl hydroxide" group refers to a "—S(=O)₂—OH" group.

A "sulfino" group refers to a "—S(=O)OH" group.

A "sulfonate" group refers to —SO₃.

An "S-sulfonamido" group refers to a "—SO₂NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—N(R$_A$)SO₂R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —NH₂).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF₃), halo($C_1$-$C_6$)alkoxy (e.g., —OCF₃), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

As understood by one of ordinary skill in the art, if a compound contains positively or negatively charged substituent groups, for example, SO₃⁻, it may also contains a negatively or positively charged counterion such that the compound as a whole is neutral.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH₂—, —CH₂CH₂—, —CH₂CH(CH₃)CH₂—, and the like. Other radical naming conventions clearly indicate that the radical is a di-radical such as "alkylene" or "alkenylene."

When two "adjacent" R groups are said to form a ring "together with the atom to which they are attached," it is meant that the collective unit of the atoms, intervening bonds, and the two R groups are the recited ring. For example, when the following substructure is present:

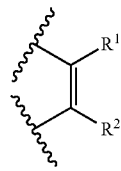

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

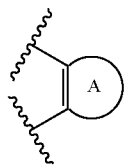

where A is an aryl ring or a carbocyclyl containing the depicted double bond.

Labeled Nucleotides

The dye compounds described herein are suitable for attachment to substrate moieties. Substrate moieties can be virtually any molecule or substance to which the fluorescent dyes described herein can be conjugated and, by way of non-limiting example, may include nucleosides, nucleotides, polynucleotides, carbohydrates, ligands, particles, solid surfaces, organic and inorganic polymers and combinations or assemblages thereof, such as chromosomes, nuclei, living cells and the like. The dyes can be conjugated by an optional linker by a variety of means including hydrophobic attraction, ionic attraction and covalent attachment. Particularly the dyes are conjugated to the substrate by covalent attachment. More particularly the covalent attachment is by means of a linker group. In some instances, such labeled nucleotides are also referred to as "modified nucleotides."

A particular useful application of the new fluorescent dyes with long Stokes shift as described herein is for labeling biomolecules, for example, nucleotides or oligonucleotides. Some embodiments of the present application are directed to a nucleotide or oligonucleotide labeled with the new fluorescent compounds as described herein.

Fluorescent dye molecules with improved fluorescence properties (such as Stokes shift, fluorescence intensity, position of fluorescence maximum and shape of fluorescence band) can improve the speed and accuracy of nucleic acid sequencing. Stokes Shift is a key aspect in the detection of the fluorescence in biological applications. For example, the detection of emitted light can be difficult to distinguish from the excitation light when using fluorophores with absorption and fluorescence max very close to each other (i.e., small Stokes shift), because the excitation and emission wavelengths greatly overlap. In contrast, fluorophores with large Stokes shifts are easy to distinguish because of the greater separation between the excitation and emission wavelengths. The Stokes shift is especially critical in multiplex fluorescence applications, because the emission wavelength of one fluorophore may overlap, and therefore excite, another fluorophore in the same sample. In addition, fluorescence signal intensity is especially important when measurements are made in water based biological buffers and/or at higher temperature as fluorescence of most dyes is significantly lower at such conditions. Moreover, the nature of the base to which a dye is attached also affects the fluorescence maximum, fluorescence intensity and other spectral dye properties. The sequence specific interactions between the fluorescent dye and the nucleobase can be tailored by specific design of the fluorescent dyes. Optimization of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

The attachment to the biomolecules may be via $R^6$, $R^8$, $R^{10a}$, $R^{10b}$, $R^{10c}$ or $R^{10}$ moiety of the compound of Formula (I) or Formula (II). In some embodiments, $R^6$, $R^8$, $R^{10a}$, $R^{10b}$, $R^{10c}$ or $R^{10}$ is a substituted alkyl, for example alkyl substituted with carboxyl (i.e., —$CO_2H$) or an activated form of carboxyl group, for example, amide or ester, which may be used for attachment to the amino group of the biomolecules. In one embodiment, $R^6$, $R^8$, $R^{10a}$, $R^{10b}$, $R^{11c}$ or $R^{10}$ may contain an activated ester or amide residue most suitable for further amide/peptide bond formation. The term "activated ester" as used herein, refers to a carboxyl group derivative which is capable of reacting in mild conditions, for example, with a compound containing an amino group. Non-limiting examples of activated esters include but not limited to p-nitrophenyl, pentafluorophenyl and succinimido esters.

In some embodiments, the dye compounds may be covalently attached to oligonucleotides or nucleotides via the nucleotide base. For example, the labeled nucleotide or oligonucleotide may have the label attached to the $C_5$ position of a pyrimidine base or the $C_7$ position of a 7-deaza purine base through a linker moiety. The labeled nucleotide or oligonucleotide may also have a 3'-OH blocking group covalently attached to the ribose or deoxyribose sugar of the nucleotide.

Linkers

The dye compounds as disclosed herein may include a reactive linker group at one of the substituent positions for covalent attachment of the compound to another molecule. Reactive linking groups are moieties capable of forming a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Non-limiting examples of linker groups include those disclosed in PCT Publication No. WO2004/018493 (herein incorporated by reference), which connect the bases of nucleotides to labels such as, for example, the new fluorescent compounds described herein. These linkers may be cleaved using water-soluble phosphines or water-soluble transition metal catalysts formed from a transition metal and at least partially water-soluble ligands. In aqueous solution the latter form at least partially water-soluble transition metal complexes. Additional suitable linkers that may be used include those disclosed in PCT Publication No. WO2004/018493 and WO 2007/020457 (both of which are herein incorporated by references. It was discovered that by altering, and in particular increasing, the length of the linker between a fluorescent dye (fluorophore) and the guanine base, by introducing a polyethylene glycol spacer group, it is possible to increase the fluorescence intensity compared to the same fluorophore attached to the guanine base through other linkages known in the art. The design of the linkers, and especially their increased length, also allows improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —((CH$_2$)$_2$O)$_n$—, wherein n is an integer between 2 and 50, as described in WO 2007/020457.

Nucleosides and nucleotides may be labeled at sites on the sugar or nucleobase. As understood by one of ordinary skill in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono-, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

The dye may be attached to any position on the nucleotide base, through a linker, provided that Watson-Crick base pairing can still be carried out. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the new fluorescent dyes described herein may have the formula:

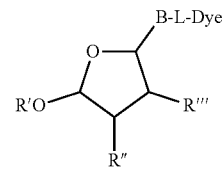

where Dye is a dye compound, B is a nucleobase, such as, for example uracil, thymine, cytosine, adenine, guanine and the like and L is an optional linker group which may or may not be present. R' can be H, monophosphate, diphosphate, triphosphate, thiophosphate, a phosphate ester analog, —O— attached to a reactive phosphorous containing group or —O— protected by a blocking group. R" can be H, OH, a phosphoramidite or a 3'-OH blocking group and R'" is H or OH; where R" is phosphoramidite, R' is an acid-cleavable hydroxyl protecting group which allows subsequent monomer coupling under automated synthesis conditions.

In some instances, the blocking group is separate and independent of the dye compound, i.e. not attached to it. Alternatively, the dye may comprise all or part of the 3'-OH blocking group. Thus R" can be a 3'-OH blocking group which may or may not comprise the dye compound. In additional alternative embodiments, there is no blocking group on the 3' carbon of the pentose sugar and the dye (or dye and linker construct) attached to the base, for example, can be of a size or structure sufficient to act as a block to the incorporation of a further nucleotide from a point other than the 3' site. Thus the block can be due to steric hindrance or can be due to a combination of size, charge and structure.

The use of a blocking group allows polymerization to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue. Non-limiting examples of 3'-OH blocking groups include those disclosed in WO 2004/018497 and WO2014/139596, which are hereby incorporated by references. For example the blocking group may be azidomethyl (—CH$_2$N$_3$) or substituted azidomethyl (e.g., —CH(CHF$_2$)N$_3$ or CH(CH$_2$F)N$_3$), or allyl.

In a particular embodiment the linker and blocking group are both present and are separate moieties which are both cleavable under substantially similar conditions. Thus deprotection and deblocking processes may be more efficient since only a single treatment will be required to remove both the dye compound and the blocking group.

The present disclosure also directs to encompassing polynucleotides incorporating dye compounds described herein. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, provided that at least one nucleotide labeled with a dye compound, according to the present application is present. Polynucleotides may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

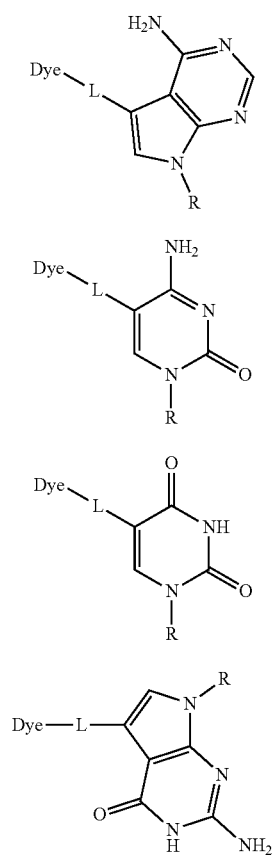

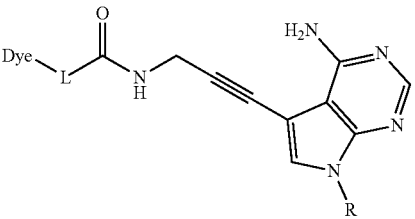

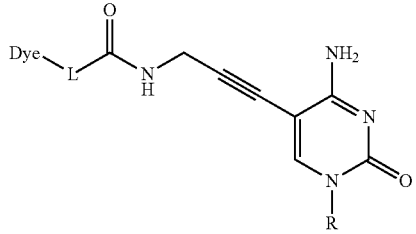

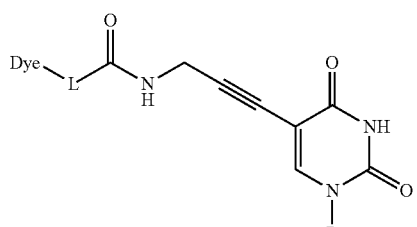

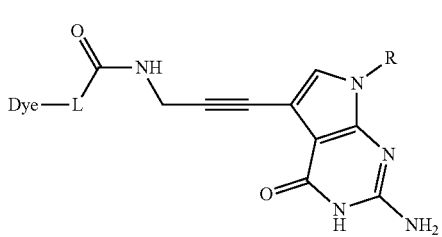

wherein: L represents a linker and R represents a sugar residue as described above.

In some embodiments, non-limiting exemplary fluorescent dye conjugates are shown below:

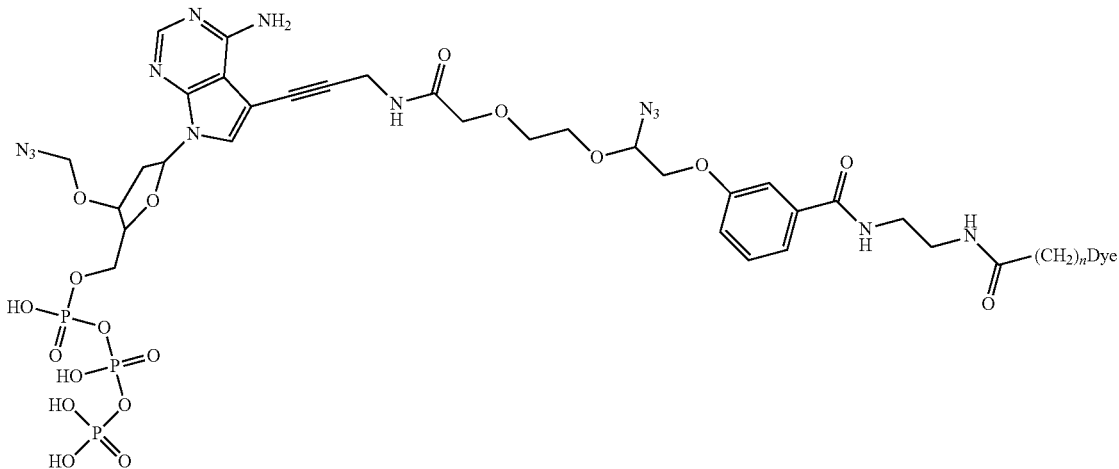

ffA-LN3-Dye

-continued

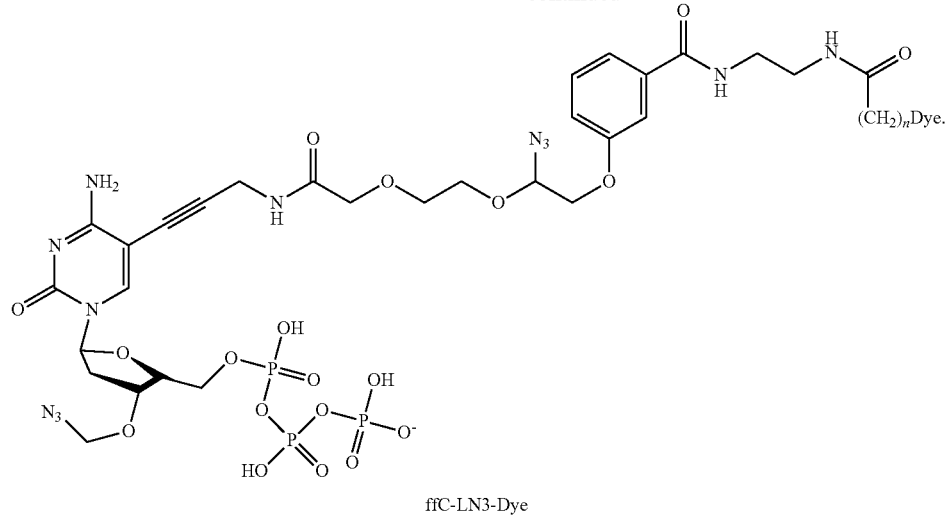

ffC-LN3-Dye

Kits

Some embodiments disclosed herein are kits including nucleosides and/or nucleotides labeled with the new fluorescent dyes described herein. Such kits will generally include at least one nucleotide or nucleoside labeled with a dye together with at least one further component. The further component(s) may be further modified or unmodified nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components or as nucleotide mixtures. In some embodiments, the kits comprise one or more nucleotides wherein at least one nucleotide is a nucleotide labeled with a new fluorescent compound described herein. The kits may comprise two or more labeled nucleotides. The nucleotides may be labeled with two or more fluorescent labels. Two or more of the labels may be excited using a single excitation source, which may be a laser.

The kits may contain four nucleotides, where the first of four nucleotides is labeled with a compound as disclosed herein, and the second, third, and fourth nucleotides are each may be labeled with a different compound, wherein each compound has a distinct fluorescence maximum and each of the compounds is distinguishable from the other three compounds. The kits may be such that two or more of the compounds have a similar absorbance maximum but different Stokes shift.

The fluorescent dye compounds, labeled nucleotides or kits described herein may be used in sequencing, expression analysis, hybridization analysis, genetic analysis, RNA analysis or protein binding assays. The use may be on an automated sequencing instrument. The sequencing instrument may contain two lasers operating at different wavelengths.

Where kits comprise a plurality, particularly two, more particularly four, nucleotides labeled with a dye compound, the different nucleotides may be labeled with different dye compounds, or one may be dark, with no dye compounds. Where the different nucleotides are labeled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two nucleotides labeled with fluorescent dye compounds are supplied in kit form, the spectrally distinguishable fluorescent dyes can be excited at the same wavelength, such as, for example by the same laser in some embodiments. When four nucleotides labeled with fluorescent dye compounds are supplied in kit form, two of the spectrally distinguishable fluorescent dyes can both be excited at one wavelength and the other two spectrally distinguishable dyes can both be excited at another wavelength in some embodiments. Particular excitation wavelengths are about 460 nm.

In some embodiments, at least one nucleotide may be labelled with a dye which excitable with two lasers with different wavelength.

In one embodiment a kit comprises a nucleotide labeled with a compound described herein and a second nucleotide labeled with a second dye wherein the dyes have a difference in absorbance maximum of at least 10 nm, particularly 20 nm to 50 nm. More particularly the two dye compounds have Stokes shifts of between 15-40 nm or between 20-40 nm. As used herein, the term "Stokes shift" is the distance between the peak absorption and peak emission wavelengths.

In a further embodiment said kit further comprises two other nucleotides labeled with fluorescent dyes wherein said dyes are excited by the lasers at about 440 nm to about 560 nm.

In an alternative embodiment, the kits may contain nucleotides where the same base is labeled with two different compounds. A first nucleotide may be labeled with a compound described herein. A second nucleotide may be labeled with a spectrally distinct compound, for example a 'red' dye absorbing at greater than 600 nm. A third nucleotide may be labeled as a mixture of the fluorescent dye compound described herein and the spectrally distinct compound, and the fourth nucleotide may be 'dark' and contain no label. In simple terms therefore the nucleotides 1-4 may be labeled 'green', 'red', 'red/green', and dark. To simplify the instrumentation further, four nucleotides can be labeled with a two dyes excited with a single laser, and thus the labeling of nucleotides 1-4 may be 'green 1', 'green 2' 'green 1/green 2', and dark.

In other embodiments the kits may include a polymerase enzyme capable of catalyzing incorporation of the nucleotides into a polynucleotide. Other components to be included in such kits may include buffers and the like. The nucleotides labeled with the new fluorescent dyes described herein, and other any nucleotide components including mixtures of different nucleotides, may be provided in the kit in a concentrated form to be diluted prior to use. In such embodiments a suitable dilution buffer may also be included.

Methods of Sequencing

Nucleotides (or nucleosides) comprising a new fluorescent dye described herein may be used in any method of analysis which requires detection of a fluorescent label attached to a nucleotide or nucleoside, whether on its own or incorporated into or associated with a larger molecular structure or conjugate. Some embodiments of the present application are directed to methods of sequencing including: (a) incorporating at least one labeled nucleotide as described herein into a polynucleotide; and (b) detecting the labeled nucleotide(s) incorporated into the polynucleotide by detecting the fluorescent signal from the new fluorescent dye attached to said modified nucleotide(s).

In some embodiments, at least one labeled nucleotide is incorporated into a polynucleotide in the synthetic step by the action of a polymerase enzyme. However, other methods of incorporating labeled nucleotides to polynucleotides, such as chemical oligonucleotide synthesis or ligation of labeled oligonucleotides to unlabeled oligonucleotides, are not excluded. Therefore, the term "incorporating" a nucleotide into a polynucleotide encompasses polynucleotide synthesis by chemical methods as well as enzymatic methods.

In all embodiments of the methods, the detection step may be carried out whilst the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with modified nucleotide(s) as described herein in a synthetic step may be subsequently used as labeled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including modified nucleotides according to the present disclosure, to form an extended target strand complementary to the template strand in the presence of a suitable polymerase enzyme. In other embodiments the synthetic step may itself form part of an amplification reaction producing a labeled double stranded amplification product comprised of annealed complementary strands derived from copying of the target and template polynucleotide strands. Other exemplary "synthetic" steps include nick translation, strand displacement polymerization, random primed DNA labeling etc. The polymerase enzyme used in the synthetic step must be capable of catalyzing the incorporation of modified nucleotides according to the present disclosure. Otherwise, the precise nature of the polymerase is not particularly limited but may depend upon the conditions of the synthetic reaction. By way of example, if the synthetic reaction is carried out using thermocycling then a thermostable polymerase is required, whereas this may not be essential for standard primer extension reactions. Suitable thermostable polymerases which are capable of incorporating the modified nucleotides according to the present disclosure include those described in WO 2005/024010 or WO 2006/120433. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the modified nucleotides or nucleosides labeled with the new fluorescent dyes with longer Stokes shift according to the present application may be used in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labeled with the modified nucleotides comprising fluorescent dyes according to the present application.

In a particular embodiment the present application provides use of modified nucleotides comprising dye compounds described herein in a polynucleotide "sequencing-by-synthesis" reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) is determined in a detection or "imaging" step. The identity of the added base may be determined after each nucleotide incorporation step. The sequence of the template may then be inferred using conventional Watson-Crick base-pairing rules. The use of the modified nucleotides labeled with dyes according to the present disclosure for determination of the identity of a single base may be useful, for example, in the scoring of single nucleotide polymorphisms, and such single base extension reactions are within the scope of this application.

In an embodiment, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides are removed and the fluorescent signal from each incorporated nucleotide is "read" optically by suitable means, such as a charge-coupled device using laser excitation and suitable emission filters. The 3'-blocking group and fluorescent dye compounds are then removed (deprotected), particularly by the same chemical or enzymatic method, to expose the nascent chain for further nucleotide incorporation. Typically, the identity of the incorporated nucleotide will be determined after each incorporation step but this is not strictly essential. Similarly, U.S. Pat. No. 5,302,509 discloses a method to sequence polynucleotides immobilized on a solid support. The method relies on the incorporation of fluorescently labeled, 3'-blocked nucleotides A, G, C and T into a growing strand complementary to the immobilized polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 2001/057248 and WO 2005/047301. Nucleotides are added successively to the free 3'-hydroxyl group, resulting in synthesis of a polynucleotide chain in the 5' to 3' direction. The nature of the base which has been added may be determined, particularly but not necessarily after each nucleotide addition, thus providing sequence information for the nucleic acid template. The term "incorporation" of a nucleotide into a nucleic acid strand (or polynucleotide) in this context refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in PCT Publication No. WO 2000/006770, wherein polynucleotides are immobilized on a glass support by reaction between a pendant epoxide group on the glass with an internal amino group on the polynucleotide. In addition, PCT Publication No. WO2005/047301 discloses arrays of polynucleotides attached to a solid support, e.g. for use in the preparation of SMAs, by reaction of a sulfur-based nucleophile with the solid support. A still further example of solid-supported template polynucleotides is where the template polynucleotides are attached to hydrogel supported upon silica-based or other solid supports. Silica-based supports are typically used to support hydrogels and hydrogel arrays as described in PCT Publication Nos. WO 00/31148, WO 01/01143, WO02/12566, WO 03/014392, WO 00/53812 and U.S. Pat. No. 6,465,178.

A particular surface to which template polynucleotides may be immobilized is a polyacrylamide hydrogel. Polyacrylamide hydrogels are described in the prior art, some of which is discussed above. Specific hydrogels that may be used in the present application include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles for the purposes of sequencing; for example as described in U.S. Pat. No. 6,172,218. Further examples of the preparation of bead libraries where each bead contains different DNA sequences can be found in Margulies et al., Nature 437, 376-380 (2005); Shendure et al., Science. 309(5741):1728-1732 (2005). Sequencing of arrays of such beads using nucleotides as described is within the scope of the present application.

The template(s) to be sequenced may form part of an "array" on a solid support, in which case the array may take any convenient form. Thus, the method of the present disclosure is applicable to all types of "high density" arrays, including single-molecule arrays, clustered arrays and bead arrays. Modified nucleotides labeled with dye compounds of the present application may be used for sequencing templates on essentially any type of array formed by immobilization of nucleic acid molecules on a solid support, and more particularly any type of high-density array. However, the modified nucleotides labeled with the new fluorescent dyes described herein are particularly advantageous in the context of sequencing of clustered arrays.

In multi-polynucleotide or clustered arrays, distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands). Multi-polynucleotide or clustered arrays of nucleic acid molecules may be produced using techniques generally known in the art. By way of example, WO 98/44151 and WO 00/18957 both describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the modified nucleotides labeled with the new fluorescent dyes described herein.

The modified nucleotides labeled with dye compounds of the present application are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilized onto the surface of the solid support should thus be capable of being resolved by optical means. This means that, within the resolvable area of the particular imaging device used, there must be one or more distinct signals, each representing one polynucleotide.

This may be achieved wherein the spacing between adjacent polynucleotide molecules on the array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photo-bleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to PCT Publication Nos. WO 2000/006770 and WO 2001/057248. Although one application of the modified nucleotides of the present disclosure is in sequencing-by-synthesis reactions, the utility of such labeled nucleotides is not limited to such methods. In fact, the nucleotides may be used advantageously in any sequencing methodology which requires detection of fluorescent labels attached to nucleotides incorporated into a polynucleotide.

In particular, the modified nucleotides labeled with dye compounds of the present application may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So called Sanger sequencing methods, and related protocols (Sanger-type), rely upon randomized chain termination with labeled dideoxynucleotides.

Thus, the present disclosure also encompasses modified nucleotides labeled with dye compounds as described herein which are dideoxynucleotides lacking hydroxyl groups at both of the 3' and 2' positions, such modified dideoxynucleotides being suitable for use in Sanger type sequencing methods and the like.

EXAMPLES

Additional embodiments are disclosed in further detail in the following examples, which are not in any way intended to limit the scope of the claims.

Example 1 tert-Butyl 4-[3-(benzo[d]thiazol-2-yl)-6,8,8-trimethyl-2-oxo-7,8-dihydro-2H-pyrano[3,2-g]quinolin-9(6H)-yl]butanoate (Compound I-1)

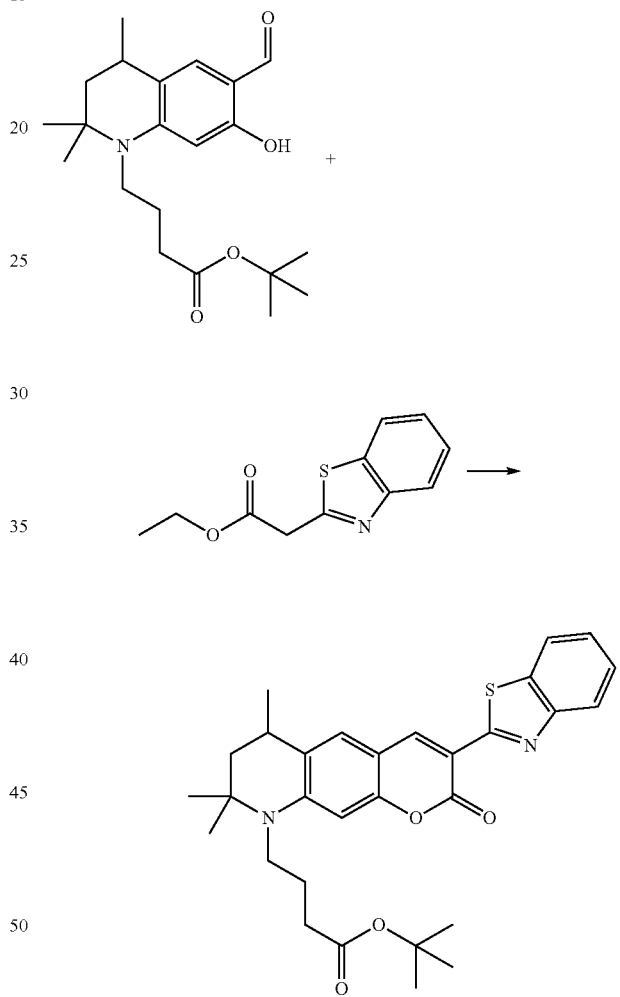

tert-Butyl 4-(6-formyl-7-hydroxy-2,2,4-trimethyl-3,4-dihydroquinolin-1(2H)-yl)butanoate (0.19 g) was dissolved in ethanol (2 mL). Ethyl 2-(benzo[d]thiazol-2-yl)acetate (0.124 g) was added and the mixture was stirred at room temperature for 15 min. Piperidine (5 µL) was added and color of the reaction mixture turned to red-yellow. Reaction mixture was left stirring at room temperature overnight. Next day the crude reaction mixture underwent aqueous workup, drying and purification by chromatography (silica gel with petroleum ether/ethyl acetate as eluent) to afford Compound I-1. Purity, structure and composition were confirmed by HPLC, NMR and LCMS. MS (DUIS): MW Calculated 518.22. Found: (−) 517 (M-1).

Example 2

4-[3-(Benzo[d]thiazol-2-yl)-6,8,8-trimethyl-2-oxo-7,8-dihydro-2H-pyrano[3,2-g]quinolin-9(6H)-yl]butanoic acid (Compound I-2)

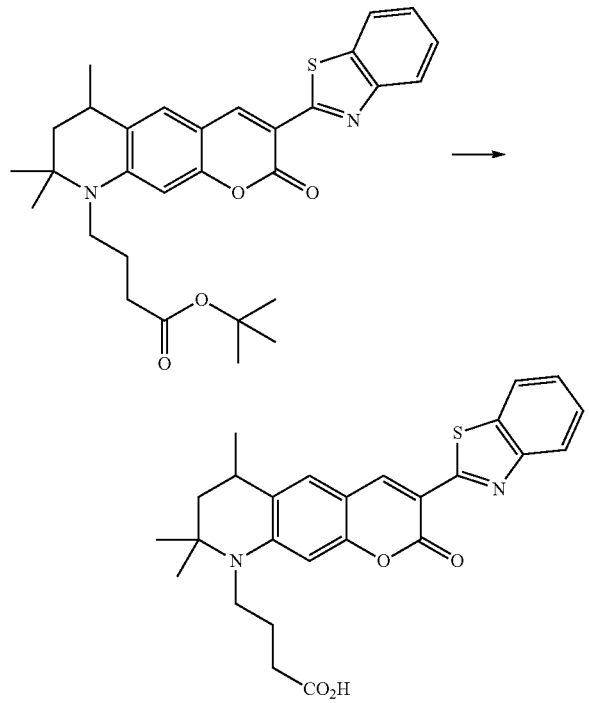

Compound I-1 (51.8 mg) was dissolved in DCM (5 mL) and trifluoroacetic acid (0.5 mL) was added via syringe and the reaction mixture was left stirring overnight at room temperature. Solvent was distilled off using rotary evaporator, the residue triturated with water (5 mL) solid filtered off and dried to afford Compound I-2. Purity, structure and composition were confirmed by HPLC, NMR and LCMS. MS (DUIS): MW Calculated 462.16. Found: (−) 461 (M−1).

Example 3 tert-Butyl 4-[3-(benzo[d]thiazol-2-yl)-6,8,8-trimethyl-2-oxo-2H-pyrano[3,2-g]quinolin-9(6H)-yl]butanoate (Compound I-3)

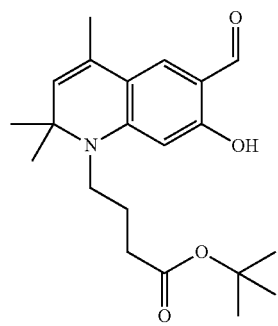

+

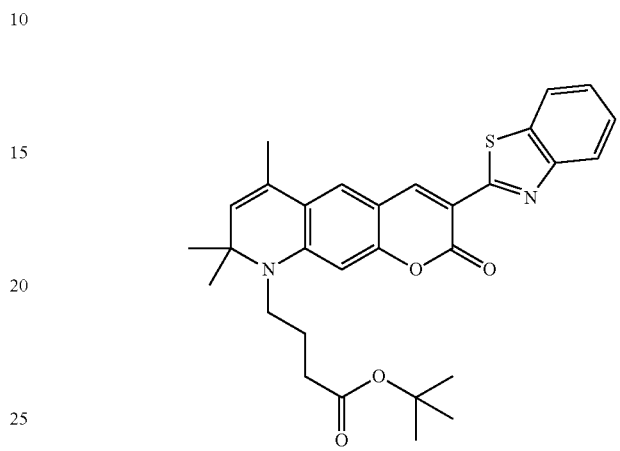

tert-Butyl 4-(6-formyl-7-hydroxy-2,2,4-trimethyl-quinolin-1(2H)-yl)butanoate (0.19 g) was dissolved in ethanol (2 mL). Ethyl 2-(benzo[d]thiazol-2-yl)acetate (0.124 g,) was added and the mixture was stirred at room temperature for 15 min. Piperidine (5 µL) was added and color of the reaction mixture turned to red-yellow. Reaction mixture was left stirring at room temperature overnight and the crude reaction mixture underwent aqueous workup, drying and purification by chromatography (silica gel with petroleum ether/ethyl acetate as eluent) to afford Compound I-3. Purity, structure and composition were confirmed by HPLC, NMR and LCMS. MS (DUIS): MW Calculated 516.22. Found: (−) 515 (M−1); (+) 517 (M+1).

Example 4

4-[3-(Benzo[d]thiazol-2-yl)-6,8,8-trimethyl-2-oxo-2H-pyrano[3,2-g]quinolin-9(6H)-yl]butanoic acid (Compound I-4)

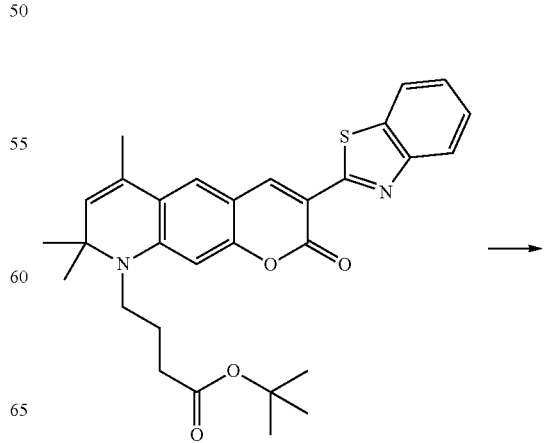

-continued

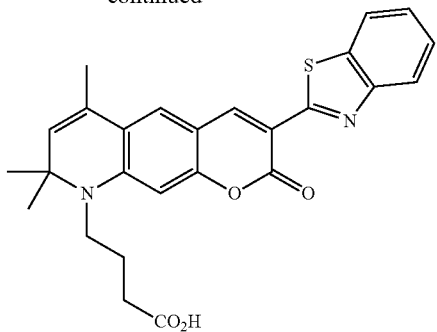

Compound I-3 (51.7 mg) was dissolved in DCM (6 mL) and trifluoroacetic acid (1 mL) was added via syringe and the reaction mixture was left stirring overnight at room temperature. Solvent was distilled off using rotary evaporator, and the residue was triturated with water (5 mL). The formed solid was filtered off and dried to afford Compound I-4. Purity, structure and composition were confirmed by HPLC, NMR and LCMS. MS (DUIS): MW Calculated 460.15.
Found: (+) 461 (M+1).

Example 5 t-Butyl 4-[3-(benzoxazolyl-2-yl)-6,8,8-trimethyl-2-oxo-7,8-dihydro-2H-pyrano[3,2-g]quinolin-9(6H)-yl]butanoate (Compound I-5)

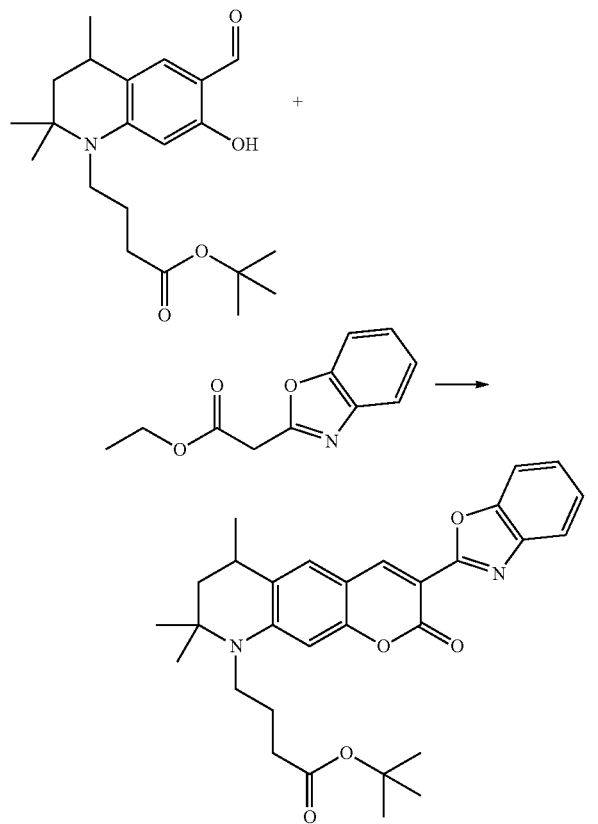

tert-Butyl 4-(6-formyl-7-hydroxy-2,2,4-trimethyl-3,4-dihydroquinolin-1(2H)-yl)butanoate (0.18 g) was dissolved in ethanol (3 mL). Ethyl 2-(benzoxazolyl)acetate (0.124 g) was added and the mixture was stirred at room temperature for 15 min. Piperidine (5 μL) was added. Color of the reaction mixture turned to red-yellow. Reaction mixture was left stirring at room temperature overnight. The crude reaction mixture underwent aqueous workup, drying and purification by chromatography (silica gel with petroleum ether/ethyl acetate as eluent) to afford Compound I-5. Purity, structure and composition were confirmed by HPLC, NMR and LCMS. MS (DUIS): MW Calculated 502.25. Found: (−) 501 (M-1).

Example 6

4-[3-Benzoxazol-2-yl)-6,8,8-trimethyl-2-oxo-7,8-dihydro-2H-pyrano[3,2-g]quinolin-9(6H)-yl]butanoic acid (Compound I-6)

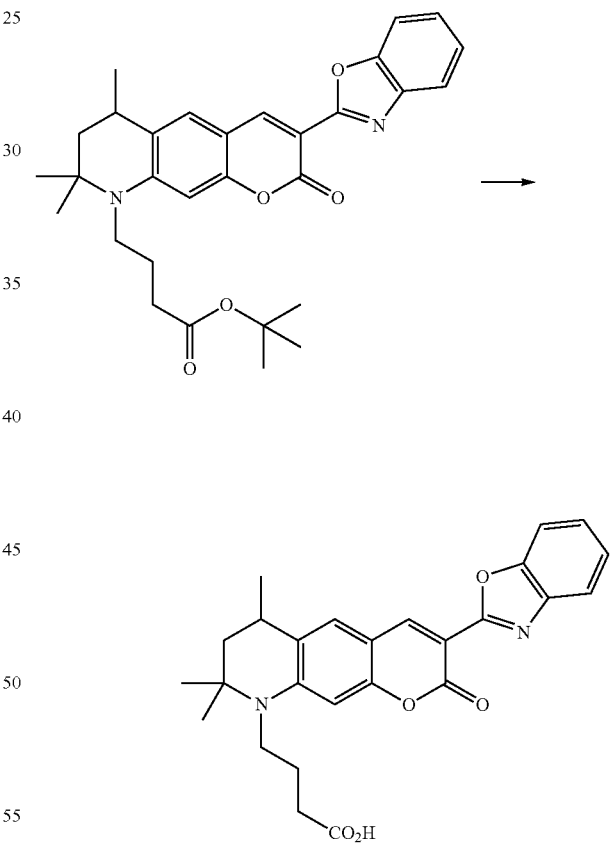

Compound I-5 (50 mg) was dissolved in DCM (5 mL) and trifluoroacetic acid (0.5 mL) was added via syringe and the reaction mixture was left stirring overnight at room temperature. Solvent was distilled off using rotary evaporator, and the residue triturated with water (5 mL). The formed solid was filtered off and dried to afford Compound I-6. Purity, structure and composition were confirmed by HPLC, NMR and LCMS. MS (DUIS): MW Calculated 446.16. Found: (−) 445 (M-1).

Example 7

Ethyl 4-[3-(benzoxazol-2-yl)-6,8,8-trimethyl-2-oxo-7,8-2H-pyrano[3,2-g]quinolin-9(6H)-yl]butanoate
(Compound I-7)

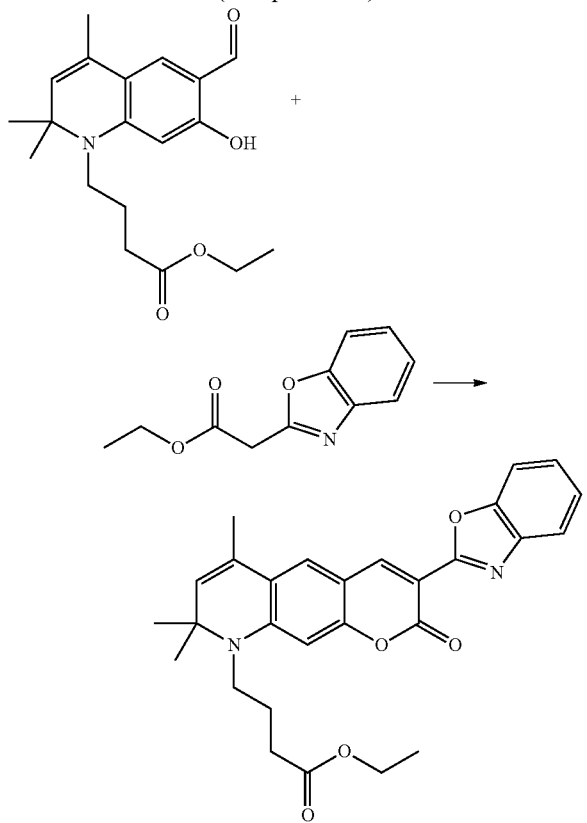

Ethyl 4-[6-formyl-7-hydroxy-2,2,4-trimethyl-3,4-quinolin-1(2H)-yl]butanoate (0.17 g) was dissolved in anhydrous ethanol (2.5 mL). Ethyl 2-(benzoxazol-2-yl)acetate (0.102 g) was added and the mixture was stirred at room temperature for 15 min. Piperidine (5 µL) was added. Reaction mixture was left stirring at room temperature overnight. The crude reaction mixture underwent aqueous workup, drying and purification by chromatography (silica gel with petroleum ether/ethyl acetate as eluent) to afford Compound I-7. Purity, structure and composition were confirmed by HPLC, NMR and LCMS. MS (DUIS): MW Calculated 472.20. Found: (+) 473 (M+1).

Example 8

4-[3-(Benzoxazol-2-yl)-6,8,8-trimethyl-2-oxo-2H-pyrano[3,2-g]quinolin-9(6H)-yl]butanoic acid
(Compound I-8)

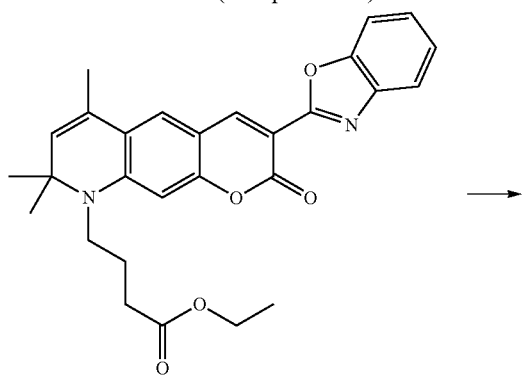

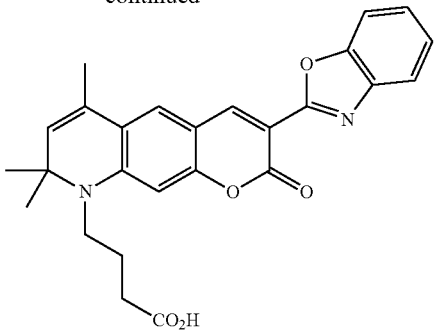

Compound I-7 (51.8 mg) was dissolved in acetic acid (2.5 mL) and hydrochloric acid (5 mL) was added and the reaction mixture was left stirring overnight at 60° C. Solvent was distilled off using rotary evaporator, and the residue was triturated with water (5 mL). Compound I-8 was filtered off and dried in vacuum. Purity, structure and composition were confirmed by HPLC, NMR and LCMS. MS (DUIS): MW Calculated 444.17. Found: (+) 445 (M+1).

Example 9

3-[4-(3-(benzoxazol-2-yl)-6,8,8-trimethyl-2-oxo-2H-pyrano[3,2-g]quinolin-9(8H)-yl)-N-(4-(tert-butoxy)-4-oxobutyl)butanamido]propane-1-sulfonic acid
(Compound I-9)

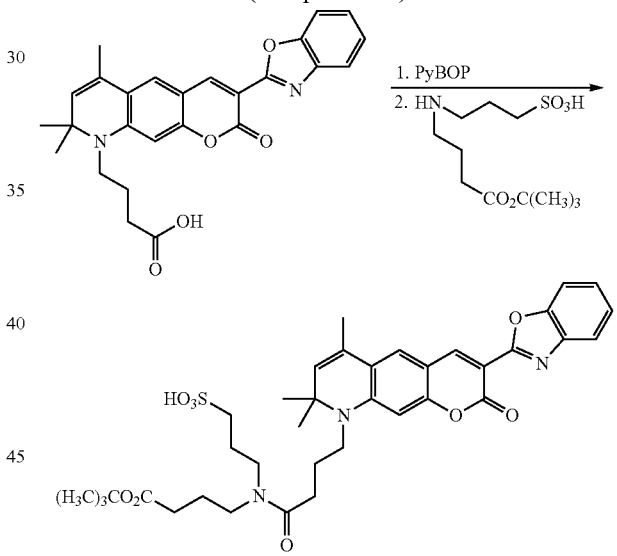

Compound I-8 (50 mg, 112 µmol) was dissolved in dimethylformamide (1 mL) and then solvent distilled off in vacuo. This operation was repeated two more times, then dried Compound I-8 was redissolved in DMF (1 mL) at room temperature. (Benzotriazol-1-yloxy)tripyrrolidinophosphonium hexafluorophosphate (PyBOP, 1.5 eq., 64 mg, 169 µmol) was added to the flask then N,N-Diisopropylethylamine (DIPEA, 3 eq., 336 µmol, 43 mg, 58 µL) was added via micropipette. Reaction flask was sealed under nitrogen gas. After reaction was completed, the activated dye solution in DMF was mixed with 3-[(4-(tert-butoxy)-4-oxobutyl)amino]propane-1-sulfonate (1.5 eq., 224 µmol, 63 mg). More DIPEA (3 eq., 336 µmol, 43 mg, 58 µL) was added. Flask was again sealed under nitrogen gas and left overnight at room temperature. Reaction progress was monitored by TLC, HPLC and (LCMS). When reaction was complete, water (2 mL) was added, the reaction mixture was stirred for 15 min and then solvent was distilled off from the reaction mixture in vacuum at room temperature. Compound I-9 was used in next step without any farther purification.

Example 10

4-[4-(3-(Benzoxazol-2-yl)-6,8,8-trimethyl-2-oxo-2H-pyrano[3,2-g]quinolin-9(8H)-yl)-N-(3-sulfopropyl)butanamido]butanoic acid (Compound I-10)

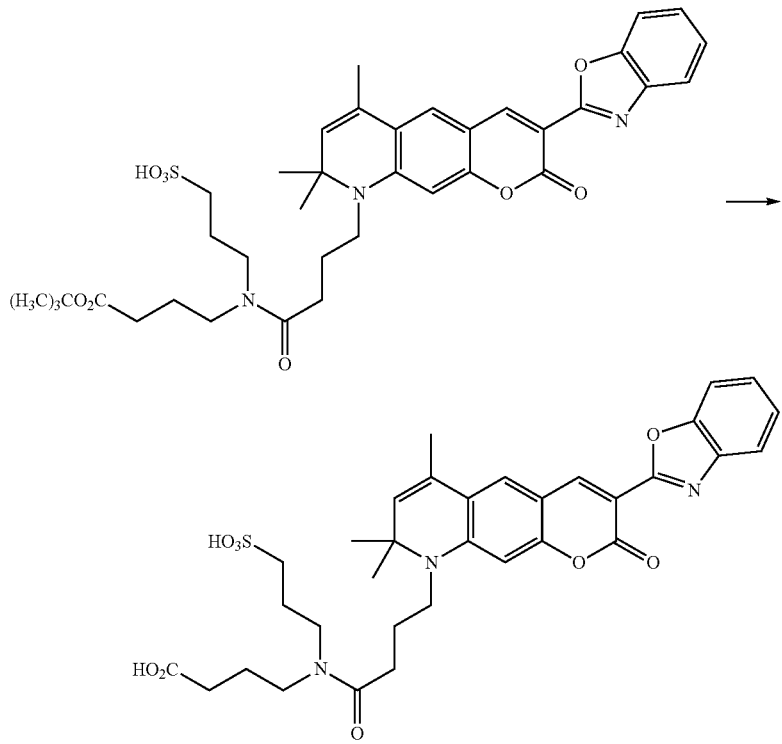

The dried crude compound I-9 was re-dissolved in dichloromethane (2 mL). Trifluoroacetic acid (0.5 mL) was added and the reaction was left stirring overnight at room temperature. The reaction was quenched with water concentrated in vacuum and then purified by preparative-HPLC. Purity, structure and composition of the product were confirmed by HPLC, NMR and LCMS. MS (DUIS): MW Calculated 651.23. Found: (−) 650 (M-1).

Example 11

4-[3-(Benzoxazol-2-yl)-8,8-dimethyl-2-oxo-6-(sulfomethyl)-2H-pyrano[3,2-g]quinolin-9(8H)-yl)butanoic acid (Compound I-11)

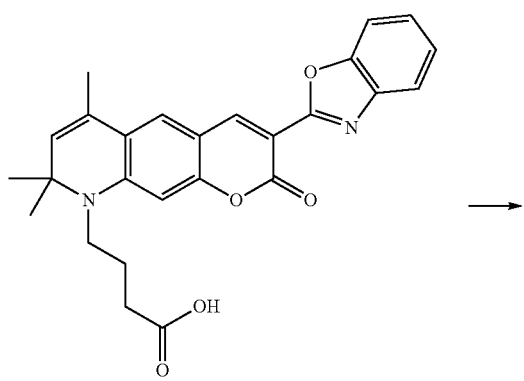

-continued

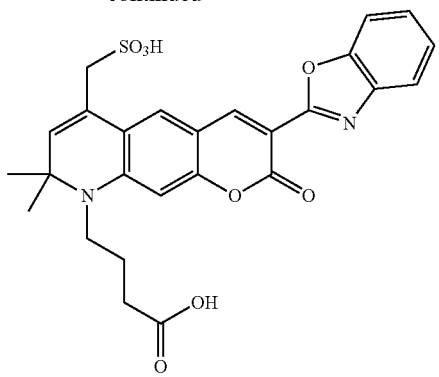

Sulfuric acid (2.5 mL) was cooled down to about 5° C. then compound I-8 (45 mg) was added and the reaction mixture was stirred at 20-25° C. for 1 h. Then reaction mixture was kept at room temperature overnight. Reaction mixture was diluted slowly with anhydrous ether in presence of external cooling. Precipitate was filtered off, dissolved in a mixture of water (5 mL) and acetonitrile (5 mL). Solution was filtered and purified by preparative HPLC. Purity, structure and composition of the product were confirmed by HPLC, NMR and LCMS. MS (DUIS): MW Calculated 524.13. Found: (−) 623 (M-1).

Example 12

1-[(5-carboxypentyl)-4-(11-oxo-2,3,6,7-tetrahydro-1H, 5H, 11H-pyrano[2,3-f]pyrido[3,2,1-ij]quinolin-10-yl]pyridinium bromide (Compound I-12)

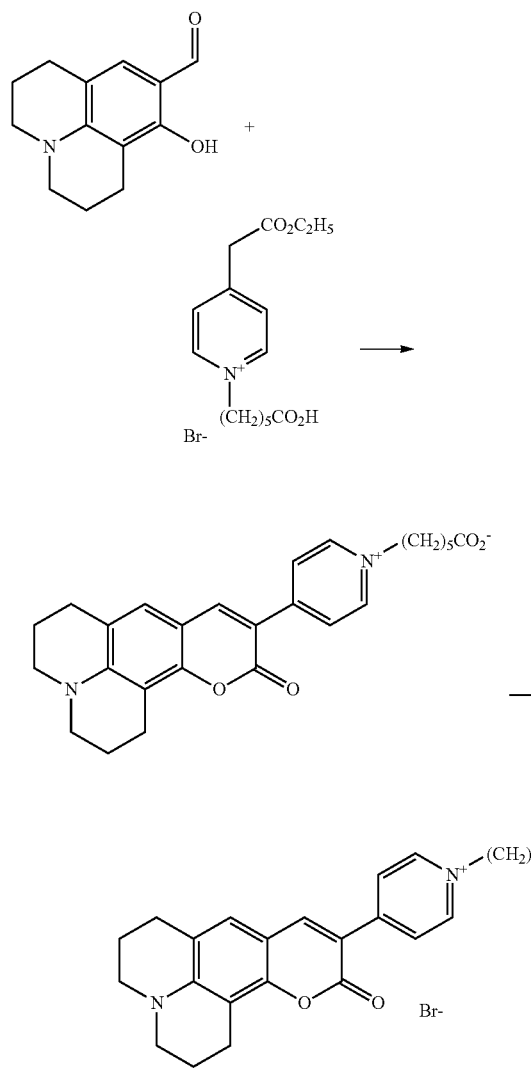

Example 13

1-(5-Carboxypentyl)-4-(1,1,7,7-tetramethyl-11-oxo-2,3,6,7-tetrahydro-1H, 5H, 11H-pyrano[2,3-f]pyrido[3,2,1-ij]quinolin-10-yl)pyridin-1-ium bromide (Compound I-13)

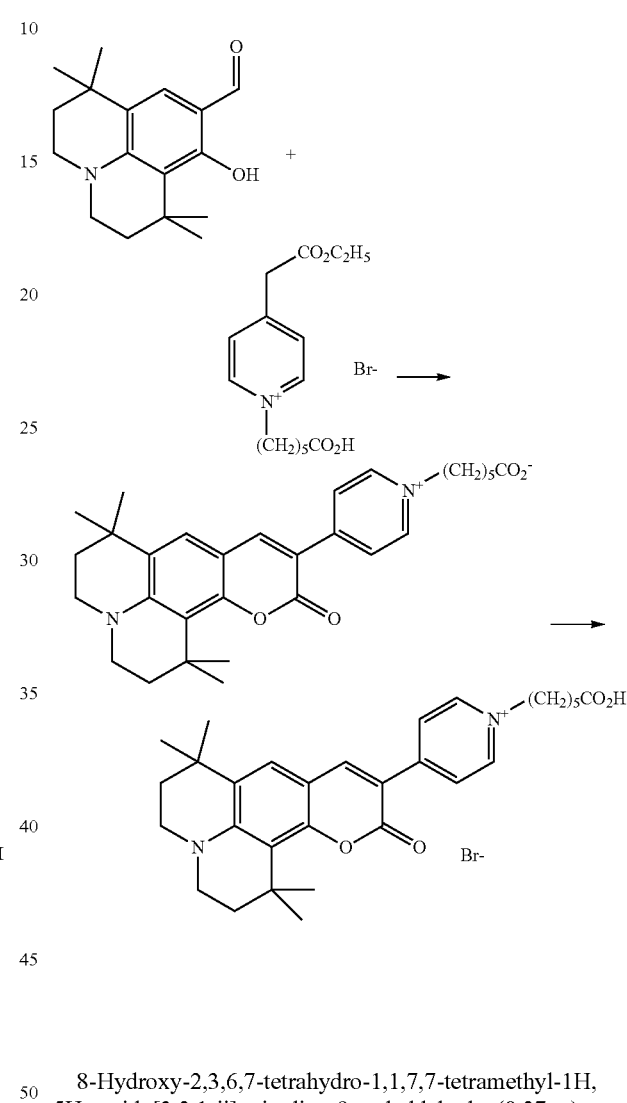

8-Hydroxy-2,3,6,7-tetrahydro-1H, 5H-pyrido[3,2,1-ij]quinoline-9-carbaldehyde (0.217 g) was dissolved in ethanol (6 mL). To this solution 1-[(5-carboxypentyl)-(4-ethoxycarbonyl)methylpyridinium bromide (0.36 g) was added and the mixture was stirred at room temperature for 15 min. Piperidine acetate solution prepared from piperidine (20 mg) and acetic acid (20 mg)/in ethanol (5 mL) was added and this reaction mixture was stirred at 60° C. for 5 hours then stirred overnight at room temperature. Solvent was distilled off and the residue was dissolved in a mixture of water (15 mL) and acetonitrile (15 mL). The resulting solution was filtered and purified by preparative HPLC. This compound was converted to more stable hydrobromide salt form to afford Compound I-12. Purity, structure and composition were confirmed by HPLC, NMR and LCMS. MS (DUIS): MW Calculated 432.20. Found: (+) 433 (M+1).

8-Hydroxy-2,3,6,7-tetrahydro-1,1,7,7-tetramethyl-1H, 5H-pyrido[3,2,1-ij]quinoline-9-carbaldehyde (0.27 g) was dissolved in ethanol (7 mL). 1-[(5-Carboxypentyl)-(4-ethoxycarbonyl)methylpyridinium bromide (0.36 g) was added and the mixture was stirred at room temperature for 30 min. Solution of piperidine acetate prepared from piperidine (20 mg) and acetic acid (20 mg) in ethanol (5 mL) was added. This reaction mixture was stirred at 60° C. for 5 hours then stirred overnight at room temperature. The solvent was distilled off and the red-colored residue was dissolved in a mixture of water (15 mL) and acetonitrile (15 mL). The resulting solution was filtered and purified by preparative HPLC. This compound was converted to the more stable hydrobromide salt form by reaction with HBr solution in acetic acid (10%, 0.3 mL) to afford Compound I-13. Purity, structure and composition were confirmed by HPLC, NMR and LCMS. MS (DUIS): MW Calculated 488.27. Found: (+) 489 (M+1).

Example 14

1-(5-Carboxypentyl)-4-(9-ethyl-2-oxo-6,7,8,9-tetrahydro-2H-pyrano[3,2-g]quinolin-3-yl)pyridin-1-ium bromide (Compound I-14)

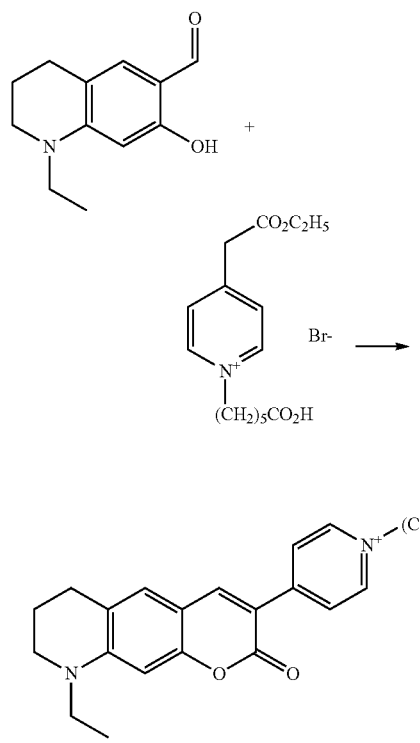

1-Ethyl-7-hydroxy-1,2,3,4-tetrahydroquinoline-6-carbaldehyde (0.2 g) was dissolved in ethanol (10 mL). 1-[(5-Carboxypentyl)-(4-ethoxycarbonyl)methylpyridinium bromide (0.36 g) was added and the mixture was stirred at room temperature for 30 min. Solution of piperidine acetate prepared from piperidine (20 mg) and acetic acid (20 mg)/in ethanol (5 mL) was added. This reaction mixture was stirred at 80° C. for 2 hours then stirred overnight at room temperature. The solvent was distilled off and the residue was dissolved in a mixture of water (10 mL) and acetonitrile (10 mL). The resulting solution was filtered and purified by preparative HPLC. This compound was converted to the more stable hydrobromide salt form by reaction with HBr solution in acetic acid (10%, 0.3 mL) to afford Compound I-14. Purity, structure and composition were confirmed by HPLC, NMR and LCMS. MS (DUIS): MW Calculated 420.20. Found: (+) 421 (M+1).

Example 15

4-[4-(9-(4-(tert-Butoxy)-4-oxobutyl)-6,8,8-trimethyl-2-oxo-6,7,8,9-tetrahydro-2H-pyrano[3,2-g]quinolin-3-yl)pyridin-1-ium-1-yl]butane-1-sulfonate (Compound I-15)

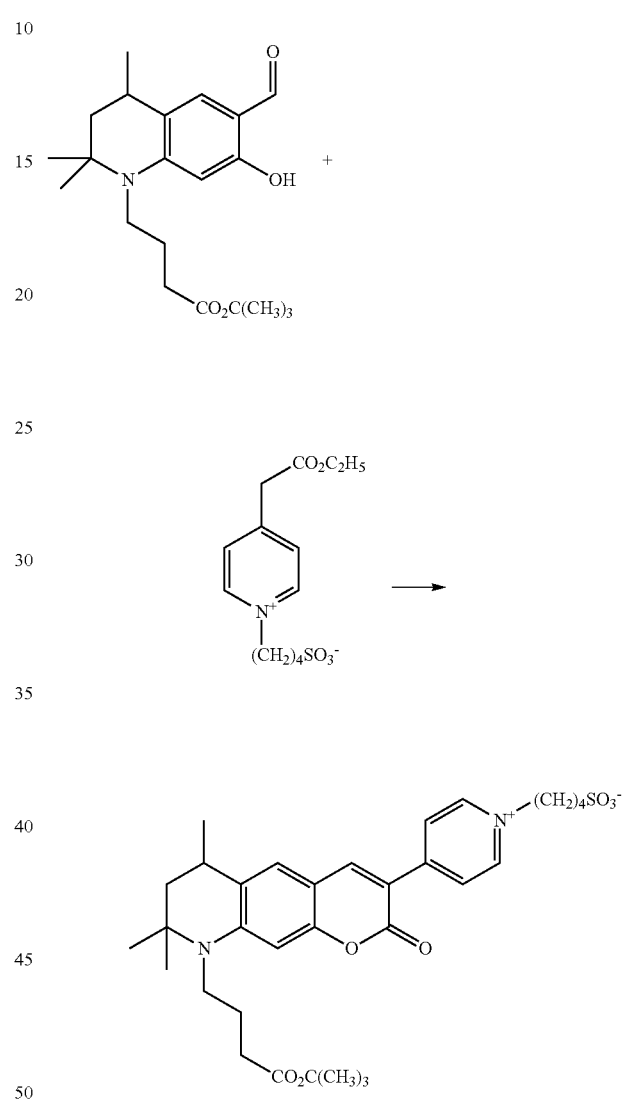

tert-Butyl 4-(6-formyl-7-hydroxy-2,2,4-trimethyl-3,4-dihydroquinolin-1(2H)-yl)butanoate (0.72 g) was dissolved in ethanol (25 mL). 4-[4-(2-Ethoxy-2-oxoethyl)pyridin-1-ium-1-yl)butane-1-sulfonate (0.60 g) was added and the mixture was stirred at room temperature for 30 min. Solution of piperidine acetate prepared from piperidine (50 mg) and acetic acid (50 mg)/in ethanol (15 mL) was added. This reaction mixture was stirred at 80° C. for 3 hours then stirred overnight at room temperature. The solvent was distilled off and the residue was dissolved in a mixture of water (20 mL) and acetonitrile (20 mL). The resulting solution was filtered and purified by preparative HPLC to afford Compound I-15. Purity, structure and composition were confirmed by HPLC, NMR and LCMS. MS (DUIS): MW Calculated 598.20. Found: (+) 599 (M+1).

Example 16

4-[4-(9-(3-Carboxypropyl)-6,8,8-trimethyl-2-oxo-6,7,8,9-tetrahydro-2H-pyrano[3,2-g]quinolin-3-yl)pyridin-1-ium-1-yl]butane-1-sulfonate (Compound I-16)

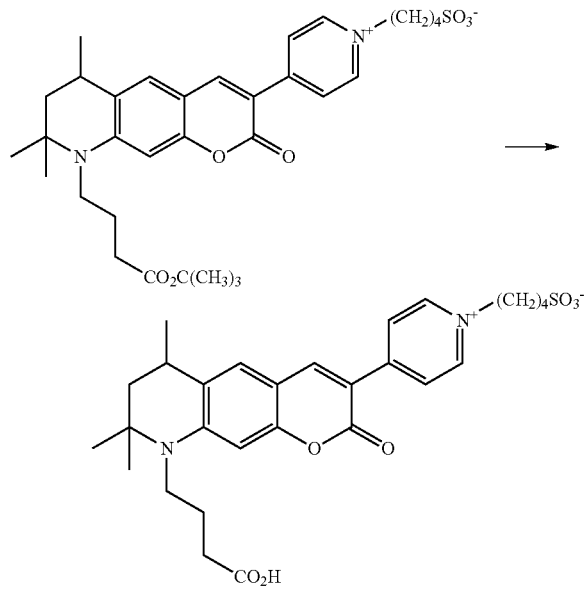

Compound I-15 was dissolved in DCM (5 ml) and TFA was added. Reaction mixture was stirred overnight at room temperature. Solvent was distilled off in vacuum. To the residue water (1.5 ml) and acetonitrile (10 mL) were added and the solvent was distilled off again to remove TFA. The remaining orange crystalline product was dissolved in a mixture of water (12 mL) and acetonitrile (12 mL). The resulting solution was filtered and purified by preparative HPLC. Purity, structure and composition were confirmed by HPLC, NMR and LCMS. MS (DUIS): MW Calculated 542.21. Found: (+) 543 (M+1).

Example 17

4-[4-(9-(4-(tert-Butoxy)-4-oxobutyl)-6,8,8-trimethyl-2-oxo-8,9-dihydro-2H-pyrano[3,2-g]quinolin-3-yl)pyridin-1-ium-1-yl]butane-1-sulfonate (Compound I-17)

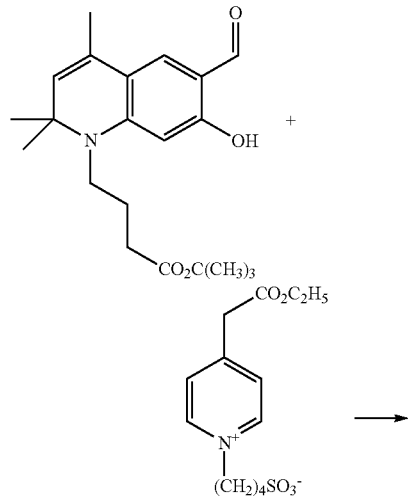

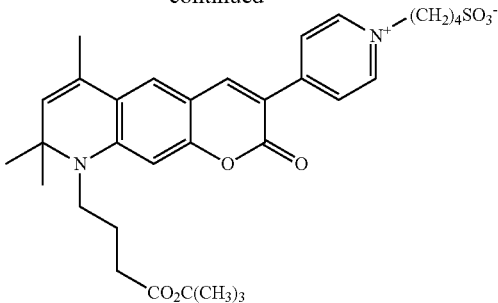

tert-Butyl 4-(6-formyl-7-hydroxy-2,2,4-trimethyl-quinolin-1(2H)-yl)butanoate (0.36 g) was suspended in ethanol (5 mL). 4-[4-(2-Ethoxy-2-oxoethyl)pyridin-1-ium-1-yl]butane-1-sulfonate (0.30 g) was added and the mixture was stirred at room temperature for 30 min. Solution of piperidine acetate prepared from piperidine (50 mg) and acetic acid (50 mg) in ethanol (15 mL) was added. This reaction mixture was stirred at 50° C. for 5 hours then stirred overnight at room temperature. Solvent was distilled off and the residue was dissolved in a mixture of water (10 mL) and acetonitrile (10 mL). The resulting solution was filtered and purified by preparative HPLC to afford Compound I-17. Purity, structure and composition were confirmed by HPLC, NMR and LCMS. MS (DUIS): MW Calculated 596.26. Found: (+) 597 (M+1).

Example 18

4-[4-(9-(3-Carboxypropyl)-6,8,8-trimethyl-2-oxo-8,9-dihydro-2H-pyrano[3,2-g]quinolin-3-yl)pyridin-1-ium-1-yl]butane-1-sulfonate (Compound I-18)

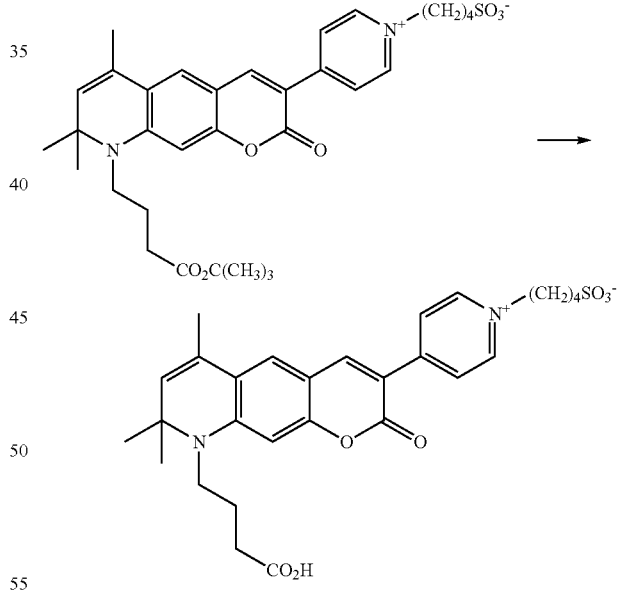

Compound I-17 was dissolved in DCM (5 ml) and TFA was added. The reaction mixture was stirred overnight at room temperature then solvent was distilled off in vacuum. To the residue water (2 ml) and acetonitrile (10 mL) were added and solvent distilled off again to remove the residue TFA. The remaining orange crystalline product was triturated with ether, filtered off and purified by preparative HPLC to afford Compound I-18. Purity, structure and composition were confirmed by HPLC, NMR and LCMS. MS (DUIS): MW Calculated 540.19. Found: (−) 539 (M−1); (+) 541 (M+1).

Example 19

4-(4-(9-(4-((4-(tert-Butoxy)-4-oxobutyl)(3-sulfopropyl)amino)-4-oxobutyl)-6,8,8-trimethyl-2-oxo-8,9-dihydro-2H-pyrano[3,2-g]quinolin-3-yl)pyridin-1-ium-1-yl)butane-1-sulfonate (Compound I-19)

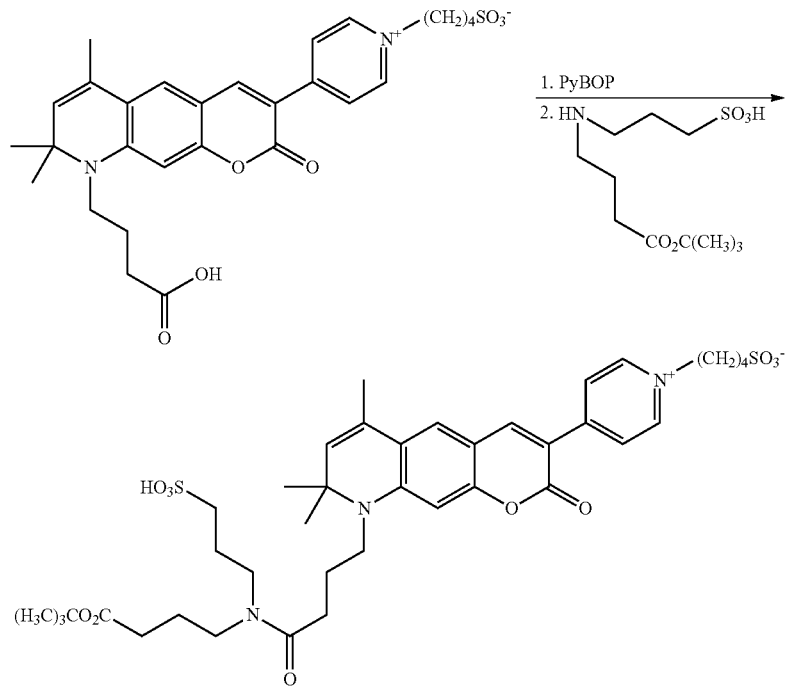

Compound I-8 (50 mg) was dissolved in DMF (1 mL) and then solvent distilled off in vacuo. This operation was repeated twice. The dried Compound I-8 was re-dissolved in DMF (1.5 mL) at room temperature. (Benzotriazol-1-yloxy)tripyrrolidinophosphonium hexafluorophosphate (PyBOP, 1.5 eq., 64 mg, 169 μmol) was added to the flask then excess of DIPEA (60 μL) was added. The reaction flask was sealed under nitrogen gas. After reaction was complete, the activated dye solution in DMF was mixed with 3-[(4-(tert-butoxy)-4-oxobutyl)amino]propane-1-sulfonate (63 mg). More DIPEA (58 μL) was added. Flask was again sealed under nitrogen gas and left overnight at room temperature. Reaction progress was monitored by TLC, HPLC and (LCMS). When reaction was complete, water (2 mL) was added. The reaction mixture was stirred for 15 min and then solvent distilled off from the reaction mixture in vacuum at room temperature to afford Compound I-19. This compound was used in next step without any further purification.

Example 20

4-(4-(9-(4-((3-Carboxypropyl)(3-sulfopropyl)amino)-4-oxobutyl)-6,8,8-trimethyl-2-oxo-8,9-dihydro-2H-pyrano[3,2-g]quinolin-3-yl)pyridin-1-ium-1-yl)butane-1-sulfonate (Compound I-20)

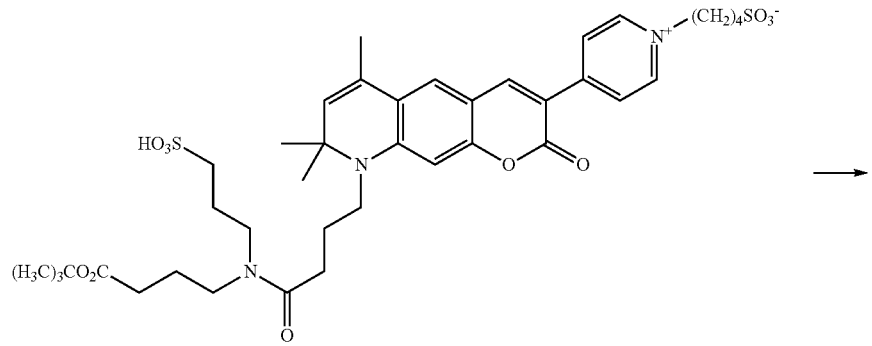

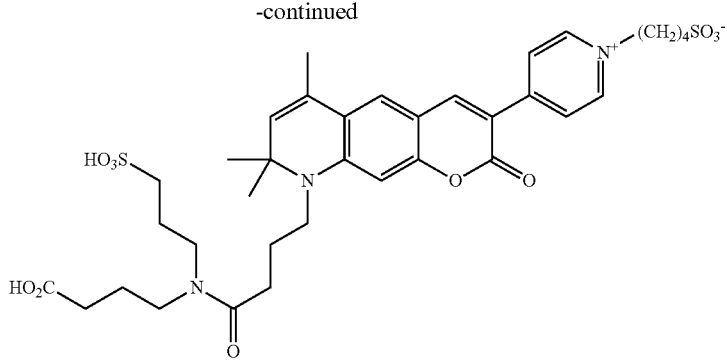

The dried compound I-19 was dissolved in dichloromethane (5 mL). Trifluoroacetic acid (0.5 mL) was added and the reaction was left stirring overnight at room temperature. The reaction was quenched with water (0.5 mL), concentrated in vacuo and then purified by preparative-HPLC. Purity, structure and composition of the product were confirmed by HPLC, NMR and LCMS. MS (DUIS): MW Calculated 747.25. Found: (−) 746 (M-1).

Example 21

1-(5-Carboxypentyl)-4-(7-(diethylamino)-2-oxo-2H-chromen-3-yl)pyridin-1-ium bromide (Compound I-21)

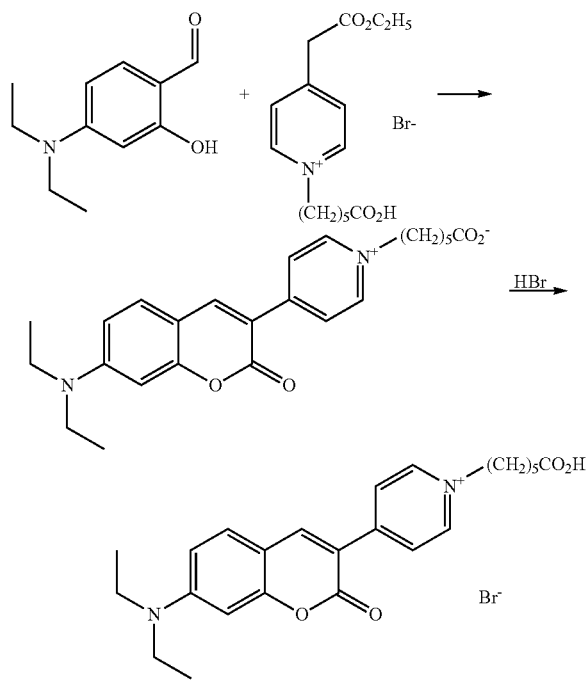

4-Diethylaminosalicilic aldehyde (0.19 g) was dissolved in ethanol (5 mL). 1-[(5-Carboxypentyl)-(4-ethoxycarbonyl) methylpyridinium bromide (0.36 g) was added and the mixture was stirred at room temperature for 30 min. Solution of piperidine acetate prepared from piperidine (10 mg) and acetic acid (10 mg)/in ethanol (5 mL) was added. This reaction mixture was stirred at 70° C. for 5 hours then stirred overnight at room temperature. The product was filtered off, suspended in HBr solution in acetic acid (20%, 1 mL). This suspension was stirred at room temperature for 2 hours and the final product was filtered off to afford the more stable HBr salt form Compound I-21. This dye was used in next step without further purification. Purity, structure and composition were confirmed by HPLC, NMR and LCMS. MS (DUIS): MW Calculated 408.20. Found: (+) 409 (M+1), 817 (2M+1).

Table 2 summarizes the yield, characterization data, and spectral properties of the new coumarin fluorescent dyes disclosed in the examples.

TABLE 2

| Compound # | Yield (%) | Spectral properties | | |
|---|---|---|---|---|
| | | Absorption nm | Fluorescence nm | Stokes Shift nm |
| I-1 | 65 | n/a | n/a | n/a |
| I-2 | 78 | 469 ($CH_3OH$) | 512 ($CH_3OH$) | 43 |
| I-3 | 84 | n/a | n/a | n/a |
| I-4 | 87 | 475 ($H_2O$) | n/a | n/a |
| I-5 | 39 | 465 (EtOH) | 500 (EtOH) | 35 |
| I-6 | 54 | 459 (EtOH) 463 ($H_2O$) | 498 (EtOH) | 39 |
| I-7 | 45 | 465 (EtOH) | n/a | n/a |
| I-8 | 76 | 470 (EtOH) | 515 (EtOH) | 45 |
| I-9 | 77 | n/a | n/a | n/a |
| I-10 | 87 | 470 ($H_2O$) | 521 ($H_2O$) | 51 |
| I-11 | 45 | 470 ($H_2O$) | n/a | n/a |
| I-12 | 56 | 502 ($H_2O$) | n/a | n/a |
| I-13 | 69 | 500 ($H_2O$) | n/a | n/a |
| I-14 | 77 | 495 (EtOH) | 565 (EtOH) | 70 |
| I-15 | 59 | 500 (EtOH) | n/a | n/a |
| I-16 | 76 | 501 (EtOH) | 575 (EtOH) | 74 |
| I-17 | 78 | 510 (EtOH) | n/a | n/a |
| I-18 | 79 | 509 (EtOH) | 592 (EtOH) | 83 |
| I-19 | 53 | 512 (EtOH) | n/a | n/a |
| I-20 | 58 | 510 (EtOH) | n/a | n/a |
| I-21 | 76 | 482 (EtOH) | 555 (EtOH) | 73 |

Example 22

General Procedure for the Synthesis of Fully Functional Nucleotide Conjugates

The coumarin fluorescent dyes disclosed herein is coupled with appropriate amino-substituted nucleotide A-LN3-$NH_2$ or C-LN3-$NH_2$ after activation of carboxylic group:

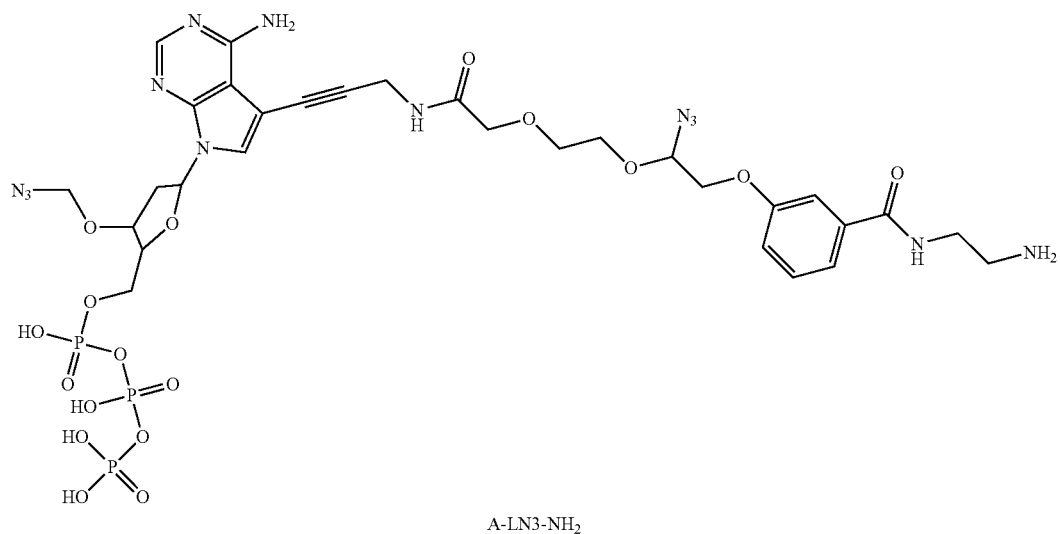

A-LN3-NH$_2$

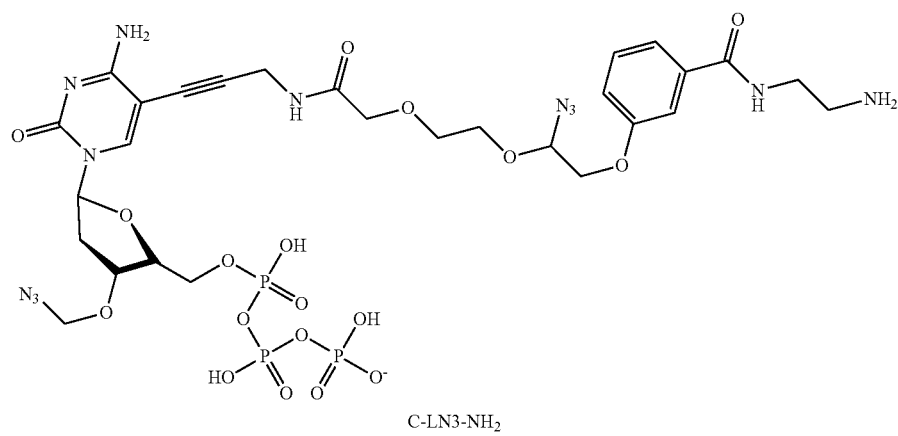

C-LN3-NH$_2$

The dye (10 µmol) is dissolved in dimethylformamide (1 mL) and then solvent is distilled off in vacuo. This procedure is repeated two more times. The dried dye is dissolved in N,N-dimethylacetamide (DMA, 0.2 mL) in a 5 mL round-bottomed flask at room temperature.

N,N,N',N'-Tetramethyl-O—(N-succinimidyl)uronium tetrafluoroborate (TSTU, 1.5 eq., 15 µmol, 4.5 mg) is added to the flask than N,N-diisopropylethylamine (DIPEA, 3 eq., 30 µmol, 3.8 mg, 5.2 µL) is added via micropipette to this solution. Reaction flask is sealed under nitrogen gas. After 15 minutes, the reaction progress is monitored by TLC (eluent H$_2$O/Acetonitrile 1:9) and HPLC. Meanwhile, solution of appropriate N-LN3-NH$_2$ derivatives (20 mM, 1.5 eq, 15 µmol, 0.75 mL) is concentrated in vacuo then re-dissolved in water (20 µL). Solution of the activated dye in DMA is transferred to the flask containing the solution of N-LN3-NH$_2$. More DIPEA (3 eq, 30 µmol, 3.8 mg, 5.2 µL) is added along with triethylamine (1 µL) Progress of coupling is monitored hourly by TLC, HPLC and LCMS.

When reaction is complete, triethylamine bicarbonate buffer (TEAB, 0.05M approx., 3 mL) is added via pipette. Initial purification of the fully functionalized nucleotide is carried out by running the quenched reaction mixture through a DEAE-Sephadex® column (Sephadex poured into an empty 25 g Biotage cartridge, solvent system TEAB/MeCN). This removes most remaining dye.

Fractions from the Sephadex column is concentrated in vacuo. The crude material is re-dissolved in the minimum volume of water and acetonitrile, before filtering through a 20 m Nylon filter. The filtered solution is purified by preparative-HPLC. Composition of prepared compounds was confirmed by LCMS.

Table 3 summarizes the structure and spectral properties of various nucleotides labelled with new coumarin dyes disclosed herein. ffA-LN3-Dye refers to a fully functionalized A nucleotide with LN3 linker and labeled with a coumarin dye disclosed herein. ffC-LN3-Dye refers to a fully functionalized C nucleotide with LN3 linker and labeled with a coumarin dye disclosed herein. The R group in each of the structures refers to the coumarin dye moiety after conjugation.

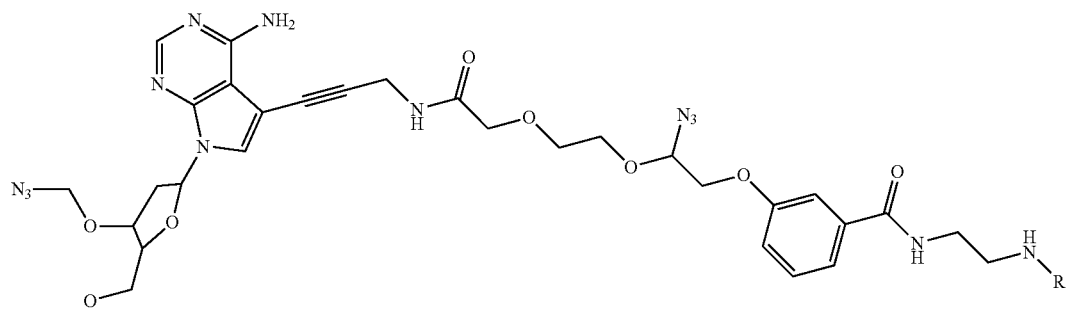
ffA-LN3-Dye
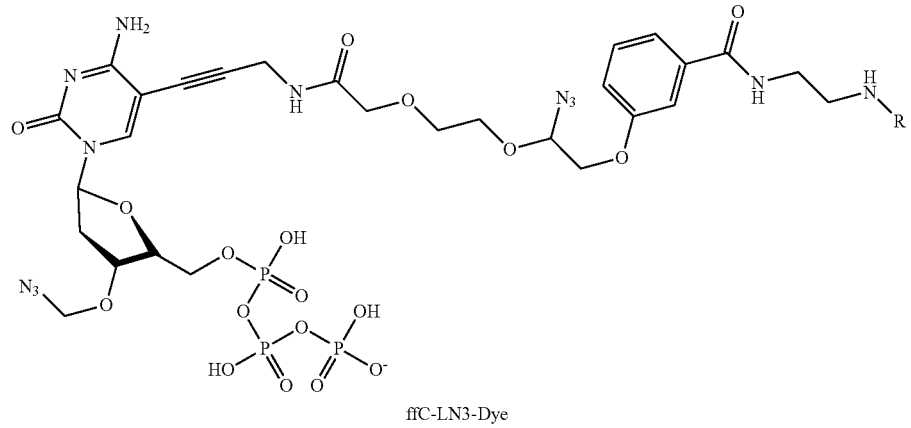
ffC-LN3-Dye
TABLE 3
| Compd. | R | Spectral properties | | |
|---|---|---|---|---|
| | | Absorption nm | Fluorescence nm | Stokes Shift nm |
| C-I-1 | [structure with benzothiazole-coumarin, (CH$_2$)$_3$CO—] | 488 (Tris) | 524 (Tris) | 36 |
| A-I-4 | [structure with benzothiazole-coumarin, (CH$_2$)$_3$CO—] | 499 (Tris) | 538 (Tris) | 39 |

TABLE 3-continued

| Compd. | R | Spectral properties | | |
|---|---|---|---|---|
| | | Absorption nm | Fluorescence nm | Stokes Shift nm |
| C-I-6 | | 473 (USM) | 507 (USM) | 34 |
| C-I-8 | | 455 (Tris) | 524 (Tris) | 69 |
| C-I-10 | | 480 (Tris) | 524 (Tris) | 43 |
| A-I-13 | | 519 (Tris) | 579 (Tris) | 80 |
| A-I-14 | | 513 (SRE) | 573 (SRE) | 60 |

TABLE 3-continued

| Compd. | R | Absorption nm | Fluorescence nm | Stokes Shift nm |
|---|---|---|---|---|
| A-I-16 | [coumarin structure with pyridinium-(CH$_2$)$_4$SO$_3^-$ substituent; N-(CH$_2$)$_3$CO— linker] | 504 (SRE) | 570 (SRE) | 66 |
| A-I-18 | [coumarin structure with pyridinium-(CH$_2$)$_4$SO$_3^-$ substituent; N-(CH$_2$)$_3$CO— linker] | 511 (Tris) | 593 (Tris) | 82 |
| A-I-20 | [coumarin structure with pyridinium-(CH$_2$)$_4$SO$_3^-$ substituent; N-linked chain to N[(CH$_2$)$_3$CO—][(CH$_2$)$_3$SO$_3$H] amide] | 514 (H$_2$O) | 593 (SRE) | 78 |
| A-DY510XL (reference) | [coumarin structure with pyridinium-(CH$_2$)$_5$CO— substituent; N-(CH$_2$)$_3$SO$_3^-$ linker] | 493 (H$_2$O) | 585 (H$_2$O) | 92 |

The efficiency of the A nucleotides labelled with the new coumarin dye I-16 with long Stokes Shift was demonstrated by comparison with appropriate A nucleotides labelled with commercial dyes DY510XL and Chromeo™ 494 (CH494). In this sequencing example, the two-channel detection method was used. With respect to the two-channel methods described herein, nucleic acids can be sequenced utilizing methods and systems described in U.S. Patent Application Publication No. 2013/0079232, the disclosure of which is incorporated herein by reference in its entirety. In the two-channel detection, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel. The scatterplots were generated by RTA2.0.93 analysis of an experiment to compare the relative intensities of fully functionalized A nucleotide labeled with 1-16, Dy510XL and Chromeo™ 494. The comparisons were made in the same run (same flow cell and sequencing reagents) by rehybridizing the sequencing primer and performing a short (26 cycles) SBS run. The scatterplots illustrated in FIG. 1 through FIG. 3 were at cycle 5 of each of the 26 cycle runs.

FIG. 1 illustrates the scatterplot of a fully functionalized nucleotide (ffN) mixture containing: A-I-16 (2 μM), C-NR440 (2 μM), dark G (2 μM) and T-NR550S0 (1 μM) in incorporation buffer with Po1812 (Blue exposure (Chan 1) 500 ms, Green exposure (Chan 2) 1000 ms; Scanned in Scanning mix).

Figure 2:
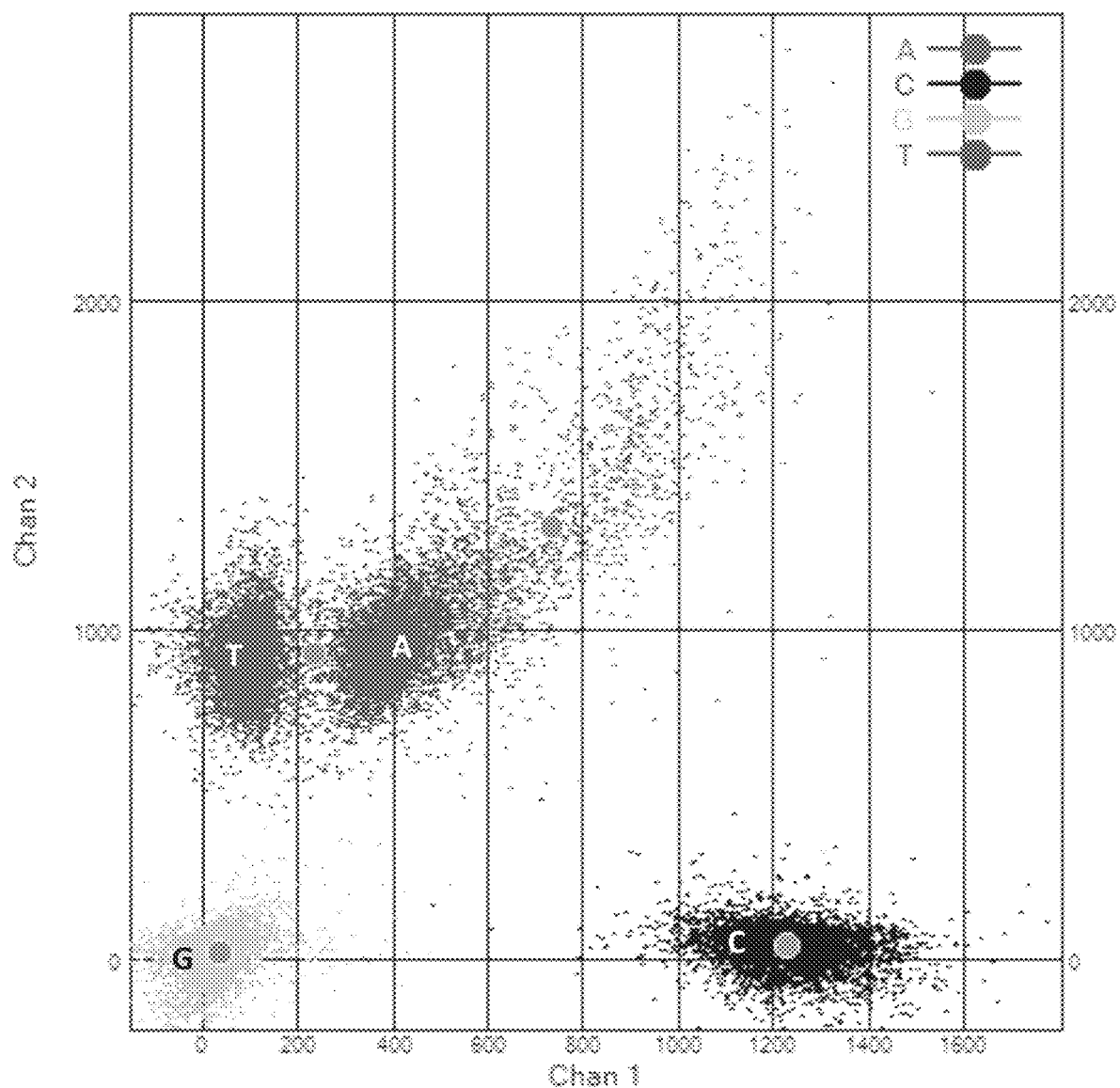
FIG. 2 illustrates the usability of the A-nucleotide labeled with a commercial fluorescent dye DY510XL with long Stokes shift for sequencing analysis.

FIG. 2 illustrates the scatterplot of a ffN mixture containing: A-DY510XL (2 μM), C-NR440 (2 μM), darkG (2 μM) and T-NR550S0 (1 μM) in incorporation buffer with Po1812 (Blue exposure (Chan 1) 500 ms, Green exposure (Chan 2) 1000 ms; Scanned in SRE).

Figure 3:
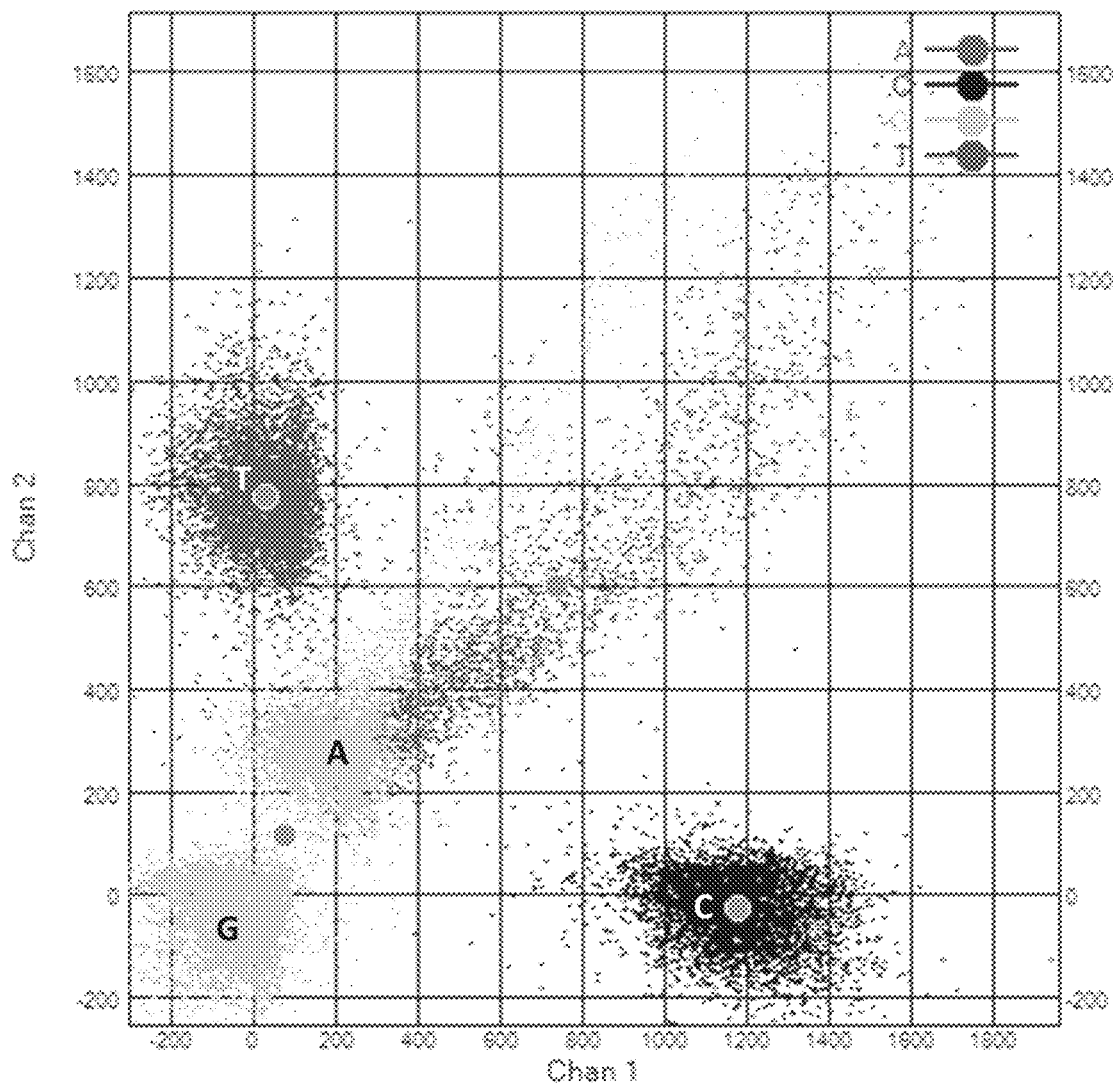
FIG. 3 illustrates the usability of the A-nucleotide labeled with a commercial fluorescent dye Chromeo494 with long Stokes shift for sequencing analysis.

FIG. 3 illustrates the scatterplot of a ffN mixture containing: A-CH494 (2 μM), C-NR440 (2 μM), darkG (2 μM) and T-NR550S0 (1 µM) in incorporation buffer with Po1812 (Blue exposure (Chan 1) 500 ms, Green exposure (Chan 2) 1000 ms; Scanned in Scanning mix).

In each of FIGS. 1-3, "G" nucleotide is unlabeled and shown as the lower left cloud ("dark G"). The signal from the new coumarin dye I-16, DY510XL, and CH494 labeled "A" nucleotide is shown as the upper right cloud in FIGS. 1, 2, and 3 respectively. The signal from the NR550S0 dye labeled "T" nucleotide is indicated by the upper left cloud, and NR440 dye labeled "C" nucleotide signal is indicated by the lower right cloud. The X-axis shows the signal intensity for one channel and the Y-axis shows the signal intensity for the other channel. It shows that the fully functional A-nucleotide conjugates labeled with dye I-16 provides sufficient signal intensities and substantially better clouds separation as compared to commercial long Stokes Shift dyes DY510XL and CH494. The structure of NR440 is disclosed in U.S. provisional application No. 62/402,635.

What is claimed is:

1. A compound of Formula (I), or a salt, or a mesomeric form thereof:

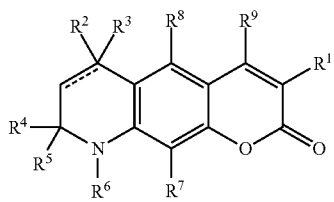

(Ia)

wherein $R^1$ is

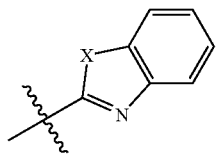

and wherein $R^1$ is substituted with one or more substituents selected from the group consisting of substituted alkyl, alkenyl, alkynyl, haloalkyl, haloalkoxy, alkoxyalkyl, amino, aminoalkyl, cyano, hydroxy, hydroxyalkyl, C-carboxy, O-carboxy, C-amido, N-amido, nitro, sulfonyl, sulfo, sulfino, sulfonate, S-sulfonamido, and N-sulfonamido;

each $R^2$, $R^3$, $R^4$, and $R^5$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

$R^6$ is independently selected from the group consisting of H, alkyl, and substituted alkyl;

each $R^7$, $R^8$ and $R^9$ is H;

X is selected from the group consisting of O, S, $NR^{11}$ and Se;

$R^{11}$ is selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and the bond represented by a solid and dashed line ------ is selected from the group consisting of a single bond and a double bond, provided that when ------ is a double bond, then $R^3$ is absent.

2. The compound of claim 1, wherein X is O.

3. The compound of claim 1, wherein X is S.

4. The compound of claim 1, wherein $R^1$ is substituted with —C(O)OH.

5. The compound of claim 1, wherein the bond represented by a solid and dashed line ------ is a double bond, and wherein $R^2$ is H, alkyl or a substituted alkyl.

6. The compound of claim 5, wherein $R^2$ is H, methyl, or —CH$_2$—SO$_3$H.

7. The compound of claim 1, wherein the bond represented by a solid and dashed line ------ is a single bond, and wherein each of $R^2$ and $R^3$ is H, alkyl or substituted alkyl.

8. The compound of claim 7, wherein $R^2$ is H, methyl, or —CH$_2$—SO$_3$H and $R^3$ is H or methyl.

9. The compound of claim 1, wherein each of $R^4$ and $R^5$ is H or alkyl.

10. The compound of claim 1, wherein $R^6$ is alkyl or substituted alkyl.

11. The compound of claim 10, wherein $R^6$ is alkyl substituted with —C(O)O$R^{12}$ or —C(O)N$R^{13}R^{14}$, wherein $R^{12}$ is selected from the group consisting of optionally substituted alkyl, optionally substituted aryl, optionally substituted heteroaryl, and optionally substituted 3 to 7 membered cycloalkyl, and wherein each $R^{13}$ and $R^{14}$ is independently selected from H, optionally substituted alkyl, optionally substituted aryl, optionally substituted heteroaryl and optionally substituted 3 to 7 membered cycloalkyl.

12. A nucleotide or oligonucleotide labeled with a compound according to claim 1.

13. The labeled nucleotide or oligonucleotide of claim 12, wherein the compound is attached to the C5 position of a pyrimidine base or the C7 position of a 7-deaza purine base of the nucleotide or oligonucleotide through a linker moiety.

14. The labeled nucleotide or oligonucleotide of claim 12, further comprising a 3'-OH blocking group covalently attached to the ribose or deoxyribose sugar of the nucleotide or oligonucleotide.

15. A kit comprising one or more nucleotides wherein at least one nucleotide is a labeled nucleotide claim 12.

16. The kit of claim 15, comprising two or more labeled nucleotides and wherein two of the labeled nucleotides are excited using a single laser.

17. A method of sequencing comprising incorporating a nucleotide according to claim 12 in a sequencing assay.

18. The method of claim 17, further comprising detecting the nucleotide.

19. The method of claim 17, wherein the sequencing assay is performed on an automated sequencing instrument, and wherein the automated sequencing instrument comprises two light sources operating at different wavelengths.

20. The compound of claim 4, wherein the bond represented by a solid and dashed line ------ is a double bond, and wherein $R^2$ is H, alkyl or a substituted alkyl.

21. The compound of claim 20, wherein each of $R^4$ and $R^5$ is H or alkyl, and $R^6$ is alkyl.

22. The compound of claim 4, wherein the bond represented by a solid and dashed line ------ is a single bond, wherein $R^2$ is H, alkyl or a substituted alkyl, and wherein $R^3$ is H or alkyl.

23. The compound of claim 22, wherein each of $R^4$ and $R^5$ is H or alkyl, and $R^6$ is alkyl.

\* \* \* \* \*

UNITED STATES PATENT AND TRADEMARK OFFICE
CERTIFICATE OF CORRECTION

PATENT NO. : 10,533,211 B2
APPLICATION NO. : 16/282783
DATED : January 14, 2020
INVENTOR(S) : Nikolai Nikolaevich Romanov Page 1 of 2

It is certified that error appears in the above-identified patent and that said Letters Patent is hereby corrected as shown below:

In the Specification

In Column 3, Lines 56-58, delete " 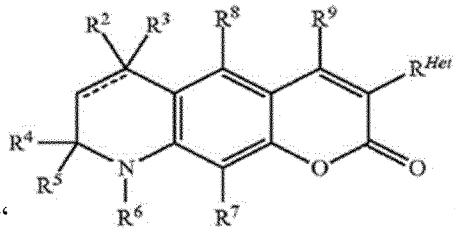 " and insert 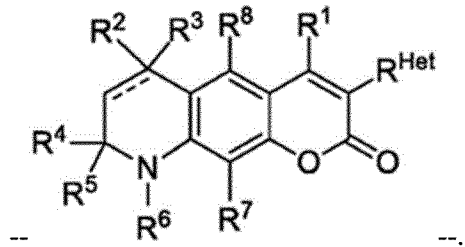 -- --.

In Column 11, Line 22, delete "(1-2)" and insert --(I-2)--.

In Column 11, Line 34, delete "(1-2)" and insert --(I-2)--.

In Column 12, Line 37, delete "1-20" and insert --I-20--.

In Column 12, Line 38, delete "1-32" and insert --I-32--.

In Column 27, Line 12, delete "(11-1)" and insert --(II-1)--.

In Column 27, Line 12, delete "(11-2)" and insert --(II-2)--.

In Column 28, Line 60, delete "$C_{14}$" and insert --$C_{1-4}$--.

Signed and Sealed this
Fifth Day of May, 2020

Andrei Iancu
*Director of the United States Patent and Trademark Office*

CERTIFICATE OF CORRECTION (continued)
U.S. Pat. No. 10,533,211 B2

In Column 30, Line 33, delete "isoquinlinyl" and insert --isoquinolinyl--.

In Column 30, Line 45, delete "isoxazollylalkyl" and insert --isoxazolylalkyl--.

In Column 31, Lines 23-24, delete "pyrrolidionyl," and insert --pyrrolidinyl,--.

In Column 31, Line 54, delete "$SO_3$" and insert --$SO_3^-$--.

In Column 34, Line 25, delete "$R^{11c}$" and insert --$R^{10c}$--.

In Column 34, Line 36, delete "$C_5$" and insert --C5--.

In Column 34, Line 37, delete "$C_7$" and insert --C7--.

In Column 35, Line 5, delete "(both" and insert --both--.

In Column 53, Line 48, delete "yl)" and insert --yl--.

In Column 55, Line 1, delete "(11" and insert --11--.

In Column 58, Line 55, delete "yl)" and insert --yl]--.

In Column 60, Line 16, delete "yl)" and insert --yl]--.

In Column 63, Line 64, delete "Diethylaminosalicilic" and insert --Diethylaminosalicylic--.

In Column 66, Line 55, delete "20 m" and insert --20 μm--.

In Column 67, Lines 40-45 (Approx.), Table 3, delete "C-I-I" and insert --C-I-1--.

In Column 71, Line 67, delete "1-16" and insert --I-16--.

In Column 72, Line 58, delete "Po1812" and insert --Pol812--.

In Column 72, Line 63, delete "Po1812" and insert --Pol812--.

In Column 73, Line 1, delete "Po1812" and insert --Pol812--.

In the Claims

In Column 74, Line 47, Claim 15, delete "nucleotide claim 12" and insert --nucleotide of claim 12--.